(12) United States Patent
Woo et al.

(10) Patent No.: US 6,878,695 B2
(45) Date of Patent: Apr. 12, 2005

(54) COMPOSITIONS COMPRISING CYCLODEXTRIN DERIVATIVES

(75) Inventors: Ricky Ah-Man Woo, Hamilton, OH (US); Hirotaka Uchiyama, Symmes Township, OH (US); Steven Reece, West Chester, OH (US); Dean Larry DuVal, Lebanon, OH (US); Heather Ann Schaeffer, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/855,329

(22) Filed: May 15, 2001

(65) Prior Publication Data

US 2001/0056080 A1 Dec. 27, 2001

Related U.S. Application Data

(60) Provisional application No. 60/204,164, filed on May 15, 2000.

(51) Int. Cl.[7] .................... A61K 31/70; A61K 31/715; A61K 9/127; A61K 9/14
(52) U.S. Cl. .................... 514/58; 514/25; 424/488; 536/46
(58) Field of Search .................... 514/25, 58, 70.13; 536/46, 103; 424/488, 76

(56) References Cited

U.S. PATENT DOCUMENTS

| | | | |
|---|---|---|---|
| 4,638,058 A | | 1/1987 | Brandt et al. |
| 4,678,598 A | | 7/1987 | Ogino et al. |
| 4,727,064 A | | 2/1988 | Pitha |
| 5,534,165 A | | 7/1996 | Pilosof et al. |
| 5,578,563 A | * | 11/1996 | Trinh et al. ................. 424/76.1 |
| 5,593,670 A | | 1/1997 | Trinh et al. |
| 5,668,097 A | * | 9/1997 | Trinh et al. ................. 510/293 |
| 5,714,137 A | | 2/1998 | Trinh et al. |
| 5,942,217 A | * | 8/1999 | Woo et al. ................. 424/76.1 |
| 5,955,093 A | | 9/1999 | Woo et al. |
| 5,968,404 A | | 10/1999 | Trinh et al. |
| 5,997,759 A | * | 12/1999 | Trinh et al. ............ 106/205.01 |
| 6,001,343 A | | 12/1999 | Trinh et al. |
| 6,001,821 A | * | 12/1999 | Pitha ........................... 514/58 |
| 6,033,679 A | | 3/2000 | Woo et al. |
| 6,106,738 A | | 8/2000 | Woo et al. |
| 6,436,442 B1 | * | 8/2002 | Woo et al. ................. 424/488 |

FOREIGN PATENT DOCUMENTS

| | | | | |
|---|---|---|---|---|
| CA | 2001667 | | 1/2000 | |
| EP | 0 636 634 A1 | | 2/1995 | |
| JP | 03 284616 | | 12/1991 | |
| JP | 03284616 | * | 12/1991 | ............ A61K/7/16 |
| JP | 3-284616 | * | 12/1991 | ............ A61K/7/16 |
| WO | WO 96/04937 | * | 2/1996 | ............ A61L/9/01 |
| WO | WO 96/04939 | | 2/1996 | |
| WO | WO 96/04940 | | 2/1996 | |

OTHER PUBLICATIONS

Authors: K. James Sasaki, Sherril D. Christian, and Edwin E. Tucker; Study of the Stability of 1:1 Complexes Between Aliphatic Alcohols and β–Cyclodextrains in Aqueous Solution; Fluid Phase Equilibria, 49; pp. 281–289, Elsevier Science Publishers B.V., 1999, The Netherlands.

Authors: Lee D. Wilson, Stephanie R. Siddall, and Ronald E. Verrall; A Spectral Displacement Study of the Binding Constants of Cyclodextrin–Hydrocarbon and–Fluorocarbon Surfactant Inclusion Complexes; Can J. Chem. vol. 75, pp. 927–933, 1997, Canada.

Authors: Mikhail V. Rekharsky and Yoshihisa Inoue, Complexation Thermodynamics of Cyclodextrains; American Chemical Society, 1998.

* cited by examiner

*Primary Examiner*—James O. Wilson
*Assistant Examiner*—Ganapathy Krishnan
(74) *Attorney, Agent, or Firm*—Jason J. Camp; Mark A. Charles; Brent M. Peebles

(57) ABSTRACT

A stable composition for removing unwanted molecules from a surface comprises low-degree of substitution cyclodextrin derivatives. The compositions are suitable for capturing unwanted molecules from inanimate surfaces, including fabrics, including carpets, and household surfaces such as countertops, dishes, floors, garbage cans, ceilings, walls, carpet padding, air filters, and the like, and from animate surfaces, including skin, hair, and the like. The compositions can further comprise cyclodextrin-compatible and -incompatible materials, and other optional ingredients.

16 Claims, No Drawings

US 6,878,695 B2

COMPOSITIONS COMPRISING CYCLODEXTRIN DERIVATIVES

CROSS-REFERENCE TO RELATED APPLICATION

This patent application claims the benefit of U.S. Provisional Application Ser. No. 60/204,164 filed May 15, 2000 by R. A. Woo, et al.

TECHNICAL FIELD

The present invention relates to stable compositions can be used for capturing unwanted molecules in a variety of contexts, preferably to control malodor including controlling malodorous molecules on inanimate surfaces, such as fabrics, including carpets, and hard surfaces including countertops, dishes, floors, garbage cans, ceilings, walls, carpet padding, air filters, and the like, and animate surfaces, such as skin and hair.

BACKGROUND OF THE INVENTION

Cyclodextrin is known to form complexes with certain materials. In many compositions, cyclodextrin is used as a carrier for active materials and thus it is desirable to form complexes between cyclodextrin and the active materials in order for the cyclodextrin to act as a carrier for the active materials. This is especially prevalent in the pharmaceautical area, where cyclodextrins have been traditionally used as carriers to deliver active materials. However, when cyclodextrin is used as a carrier for active material and is strongly complexed with the active material, the cavities of the cyclodextrin molecules are filled such that the cyclodextrin is not available to complex with other molecules.

Surfaces, especially household surfaces such as fabrics, countertops, and the like, often contain unwanted molecules, such as malodorous molecules. Cyclodextrin molecules are capable of capturing unwanted molecules from surfaces; however, cyclodextrin compositions used to treat surfaces containing unwanted molecules must have cyclodextrin that is available to complex with the unwanted molecules in order to capture and remove the unwanted molecules from the surface being treated. Compositions have been disclosed that are useful for controlling malodor on surfaces, wherein the compositions comprise uncomplexed cyclodextrin. For example, U.S. Pat. No. 5,942,217 issued Aug. 24, 1999 to Woo et al. teach compositions for controlling malodor on surfaces wherein the compositions can comprise uncomplexed cyclodextrin and materials that are cyclodextrin-compatible, such as cyclodextrin-compatible surfactants and cyclodextrin-compatible antimicrobial actives. The materials in these compositions are selected such that they do not complex with cyclodextrin in solution, thus providing available, uncomplexed cyclodextrin in solution to capture the malodor from the treated surfaces. The cyclodextrins suitable for use in the compositions disclosed in the '217 patent include derivatized cylcodextrins such as hydroxyalkyl cyclodextrins and methylated cyclodextrins. Woo et al. teach that preferred hydoxyalkyl cyclodextrins have a degree of substitution of from about 1 to about 14, and more preferably from about 1.5 to about 7, wherein the total number of OR groups per cyclodextrin is defined as the degree of substitution. Woo et al. further teach that preferred methylated cyclodextrins have a degree of substitution of from about 1 to about 18, and more preferably from about 3 to about 16.

It has thus been desired to develop optimized cyclodextrin compositions that exihibit improved performance in capturing unwanted molecules, especially malodorous molecules, by selecting appropriate cyclodextrins for: use in the compositions.

SUMMARY OF THE INVENTION

The present invention relates to compositions for capturing unwanted molecules from inanimate surfaces, including fabrics, including carpets, and hard surfaces including countertops, dishes, floors, garbage cans, ceilings, walls, carpet padding, air filters, and the like, and animate surfaces, such as skin, hair, and the like. The present invention further relates to compositions for use in a cabinet-type or bag-type apparatus for conditioning garments. The compositions herein for capturing unwanted molecules comprise low-degree of substitution cyclodextrin derivatives. The use of low-degree of substitution cyclodextrin derivatives in the present compositions provides improved performance in terms of capturing unwanted molecules from treated surfaces, as compared to similar compositions comprising higher degree of substitution cyclodextrin derivatives. The low-degree of substitution cyclodextrin derivatives in the present compositions are preferably functionally-available in the compositions in order to capture unwanted molecules from the surfaces. The present compositions can further comprise cyclodextrin-compatible and—incompatible materials, and other optional ingredients.

The low-degree of substitution cyclodextrin derivatives useful herein are preferably selected from low-degree of substitution hydroxyalkyl cyclodextrin, low-degree of substitution alkylated cyclodextrin, and mixtures thereof. Preferred low-degree of substitution hydroxyalkyl beta-cyclodextrins have an average degree of substitution of less than about 5.0, more preferably less than about 4.5, and still more preferably less than about 4.0. Preferred low-degree of substitution alkylated cyclodextrins have an average degree of substitution of less than about 6.0, more preferably less than about 5.5, and still more preferably less than about 5.0.

The present invention further relates to processes of manufacturing a composition suitable for capturing unwanted molecules wherein the composition comprises low-degree of substitution cyclodextrin derivative, cyclodextrin-incompatible material, and cyclodextrin-compatible material. The present invention also relates to methods of using the compositions of the present invention.

DETAILED DESCRIPTION OF THE INVENTION

I. Compositions

The present invention encompasses stable compositions comprising low-degree of substitution cyclodextrin derivative, wherein the cyclodextrin is preferably functionally-available cyclodextrin. The compositions can further comprise optional cyclodextrin-compatible and—incompatible materials, and other optional components.

The present compositions can be either emulsions/dispersions or clear, single-phase solutions. Compositions of the present invention for controlling malodor on fabrics are preferably clear, single-phase solutions and generally have a particle size of molecular aggregates, such as micelles and/or vesicles, of no greater than about 0.2 μm, preferably no greater than about 0.1 μm, and more preferably no greater than about 0.05 μm. Preferably, the cyclodextrin compositions of the present invention are clear. The term "clear" as defined herein means transparent or translucent, preferably transparent, as in "water clear," and have a percent transmittance of at least about 70%, preferably at least about 75%, and more preferably at least about 80% at 420 nm.

Compositions of the present invention such as detergent compositions, fabric softening compositions, shampoo compositions, hard surface cleaning compositions, and the like, are preferably emulsions/dispersions and generally have a particle size of molecular aggregates, such as micelles and/or vesicles, of greater than about 0.05 μm, preferably greater than about 0.1 μm, and more preferably greater than about 0.2 μm. These compositions can be clear, translucent, or opaque, dependent on the types and concentrations of materials in the compositions.

A. Low-Degree of Substitution Cyclodextrin Derivatives

The present compositions comprise low-degree of substitution cyclodextrin derivatives, wherein the cyclodextrin is preferably functionally-available cyclodextrin. The low-degree of substitution cyclodextrin derivatives in the present compositions are capable of exhibiting improved complexation with unwanted molecules that are present on the surfaces being treated with the present compositions. When the surfaces are treated with the present compositions, the low-degree of substitution cyclodextrin derivatives complex with the unwanted molecules, thereby more effectively removing and/or reducing the presence of the unwanted molecules on the treated surfaces, as compared to cyclodextrin derivatives having higher average degrees of substitution, even when the low-degree of cyclodextrin derivatives are used at lower levels in the compositions.

As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin, or mixtures thereof. The alpha-cyclodextrin consists of six glucose units, the beta-cyclodextrin consists of seven glucose units, and the gamma-cyclodextrin consists of eight glucose units arranged in donut-shaped rings. The specific coupling and conformation of the glucose units give the cyclodextrins a rigid, conical molecular structure with hollow interiors of specific volumes. The "lining" of each internal cavity is formed by hydrogen atoms and glycosidic bridging oxygen atoms; therefore, this surface is fairly hydrophobic. The unique shape and physical-chemical properties of the cavity enable the cyclodextrin molecules, and derivatives thereof, to absorb (form inclusion complexes with) organic molecules or parts of organic molecules which can fit into the cavity. Many unwanted molecules existing on surfaces can fit into the cavity, including many malodorous molecules. Therefore, cyclodextrins and their derivatives, and especially mixtures of cyclodextrins with different size cavities, can be used to complex with unwanted molecules, especially to control malodors caused by a broad spectrum of organic odoriferous materials, which can contain reactive functional groups. The complexation between cyclodextrin and unwanted molecules, especially malodorous molecules, occurs particularly rapidly in the presence of water. However, the extent of the complex formation can also depend on the polarity of the absorbed molecules (i.e. unwanted molecules). In an aqueous solution, strongly hydrophilic unwanted molecules (e.g. those which are highly water-soluble) tend to be only partially absorbed, if at all. Therefore, cyclodextrin does not complex effectively with some very low molecular weight organic amines and acids when they are present at low levels on wet fabrics. As the water is being removed however, e.g., the fabric is being dried off, some of the unwanted molecules, e.g. low molecular weight organic amines and acids, have more affinity and will complex with the cyclodextrins more readily.

Derivatives of cyclodextrins consist mainly of molecules wherein some of the OH groups are converted to OR groups. Cyclodextrin derivatives include, e.g., those with short chain alkyl groups such as methylated cyclodextrins, and ethylated cyclodextrins, wherein R is a methyl or an ethyl group; those with hydroxyalkyl substituted groups, such as hydroxypropyl cyclodextrins and/or hydroxyethyl cyclodextrins, wherein R is a —$CH_2$—CH(OH)—$CH_3$ or a —$CH_2CH_2$—OH group; branched cyclodextrins such as maltose-bonded cyclodextrins; cationic cyclodextrins such as those containing 2-hydroxy-3-dimethylamino)propyl ether, wherein R is $CH_2$—CH(OH)$CH_2$—N($CH_3$)$_2$ which is cationic at low pH; quaternary ammonium, e.g., 2-hydroxy-3-(trimethylammonio)propyl ether chloride groups, wherein R is $CH_2$—CH(OH)—$CH_2$—$N^+(CH_3)_3Cl$—; anionic cyclodextrins such as carboxymethyl cyclodextrins, cyclodextrin sulfates, and cyclodextrin succinylates; amphoteric cyclodextrins such as carboxymethyl/quaternary ammonium cyclodextrins; cyclodextrins wherein at least one glucopyranose unit has a 3–6-anhydro-cyclomalto structure, e.g., the mono-3–6-anhydrocyclodextrins, as disclosed in "Optimal Performances with Minimal Chemical Modification of Cyclodextrins", F. Diedaini-Pilard and B. Perly, The 7th International Cyclodextrin Symposium Abstracts, April 1994, p. 49, said references being incorporated herein by reference; and mixtures thereof. Other cyclodextrin derivatives are disclosed in U.S. Pat. No. 3,426,011, Parmerter et al., issued Feb. 4, 1969; U.S. Pat. Nos. 3,453,257; 3,453,258; 3,453,259; and 3,453,260, all in the names of Parmerter et al., and all issued Jul. 1, 1969; 3,459,731, Gramera et al., issued Aug. 5, 1969; 3,553,191, Parmerter et al., issued Jan. 5, 1971; 3,565,887, Parmerter et al., issued Feb. 23, 1971; 4,535,152, Szejtli et al., issued Aug. 13, 1985; 4,616,008, Hirai et al., issued Oct. 7, 1986; 4,678,598, Ogino et al., issued Jul. 7, 1987; 4,638,058, Brandt et al. issued Jan. 20, 1987; and 4,746,734, Tsuchiyama et al., issued May 24, 1988; all of said patents being incorporated herein by reference. Further cyclodextrin derivatives suitable herein include those disclosed in V. T. D'Souza and K. B. Lipkowitz, CHEMICAL REVIEWS: CYLCODEXTRINS, Vol. 98, No. 5 (American Chemical Society, July/August 1998), which is incorporated herein by reference. Examples of preferred water-soluble cyclodextrin derivatives suitable for use herein include hydroxypropyl alpha-cyclodextrin, methylated alpha-cyclodextrin, methylated beta-cyclodextrin, hydroxyethyl beta-cyclodextrin, hydroxypropyl beta-cyclodextrin, hydroxypropyl gamma-cyclodextrin, and methylated gamma-cyclodextrin.

As used herein, the term "degree of substitution," as it relates to cyclodextrin derivatives, refers to the total number of OR groups per cyclodextrin molecule. It is understood that commercially available cyclodextrin derivatives actually contain individual cyclodextrin molecules having varying degrees of substitution. For example, hydroxypropyl beta-cyclodextrin having an average degree of substitution of 3 still contains an amount of non-derivatized beta-cyclodextrin of about 5%, while hydroxypropyl beta-cyclodextrin having an average degree of substitution of about 5 has an amount of non-derivatized beta-cyclodextrin of less than about 1%. The term "average degree of substitution" thus relates to the average statistical distribution of individual substituted cyclodextrin molecules of a given cyclodextrin derivative. As used herein, the term "low-degree of substitution" refers to cyclodextrin derivatives in which less than about one-fourth (¼) of the OH groups of the cyclodextrin molecule have been converted to OR groups.

It has been surprisingly discovered that low-degree of substitution cyclodextrin derivatives provide significantly improved performance, as compared to similar cyclodextrin derivatives having higher degrees of substitution, in regard to capturing unwanted molecules. The improved capturing of unwanted molecules, such as malodorous molecules, by compositions comprising low-degree of substitution cyclodextrin derivatives is shown hereinafter in Example I.

The average degree of substitution of the low-degree of substitution cyclodextrin derivatives useful herein generally depends upon the particular cyclodextrin derivative. For example, hydroxyalkyl beta-cyclodextrins useful herein typically have an average degree of substitution of less than about 5.0, preferably less than about 4.5, and more preferably less than about 4.0. Alkylated cyclodextrins useful herein typically have an average degree of substitution of less than about 6.0, preferably less than about 5.5, and more preferably less than about 5.0. A highly preferred low-degree of substitution hydroxyalkyl cyclodextrin useful herein is hydroxypropyl beta-cyclodextrin having an average degree of substitution of about 3.3. A highly preferred low-degree of substitution alkylated cyclodextrin is methylated beta-cyclodextrin having an average degree of substitution of about 4.2. The preferred cyclodextrins are available, e.g., from Cerestar USA, Inc. and Wacker USA, Inc.

The compositions herein can comprise a mixture of cyclodextrins and derivatives thereof such that the mixture effectively has an average degree of substitution equivalent to the low-degree of substitution cyclodextrin derivatives described hereinbefore. Such cyclodextrin mixtures preferably comprise high-degree of substitution cyclodextrin derivatives (having a higher average degree of substitution than the low-degree substitution cyclodextrin derivatives described herein) and non-derivatized cyclodextrin, such that the cyclodextrin mixture effectively has an average degree of substitution equivalent to the low-degree of substitution cyclodextrin derivative. For example, a composition comprising a cyclodextrin mixture containing 0.1% non-derivatized beta-cyclodextrin and 0.4% hydroxypropyl beta-cyclodextrin having an average degree of substitution of about 5.5, exhibits an ability to capture unwanted molecules similar to that of a similar composition comprising low-degree of substitution hydroxypropyl beta-cyclodextrin having an average degree of substitution of about 3.3. Such cyclodextrin mixtures can typically absorb odors more broadly by complexing with a wider range of unwanted molecules, especially malodorous molecules, having a wider range of molecular sizes. Preferably at least a portion of a cyclodextrin mixture is alpha-cyclodextrin and its derivatives thereof, gamma-cyclodextrin and its derivatives thereof, and/or beta-cyclodextrin and its derivatives thereof; more preferably a mixture of alpha-cyclodextrin, or an alpha-cyclodextrin derivative, and derivatized beta-cyclodextrin, even more preferably a mixture of derivatised alpha-cyclodextrin and derivatized beta-cyclodextrin; and most preferably a mixture of hydroxypropyl alpha-cyclodextrin and hydroxypropyl beta-cyclodextrin, and/or a mixture of methylated alpha-cyclodextrin and methylated beta-cyclodextrin.

The cyclodextrins and derivatives used herein are preferably incorporated in the present compositions such that they are functionally-available. As used herein, the term "functionally-available cyclodextrin" refers to cyclodextrin that is either not complexed with other materials (e.g. uncomplexed, free cyclodextrin) or is complexed with materials that only weakly complex with cyclodextrin, e.g. weakly complexing materials that have a cyclodextrin complexation constant of less than about 5,000 $M^{-1}$, preferably less than about 4,000 $M^-$, and more preferably less than about 3,000 $M^{-1}$. So long as the cyclodextrin in the present compositions is only complexed with weakly complexing materials, the cyclodextrin will still be available to complex with unwanted molecules on the surfaces to be treated. Since the unwanted molecules will generally have a cyclodextrin complexation constant that is higher than weakly complexing materials that might be contained in the present compositions, the cyclodextrin will nevertheless be available to complex with the unwanted molecules due to the replacement of weakly complexing materials with the unwanted molecules in the cyclodextrin complexes in the present compositions.

The cavities within the functionally-available cyclodextrin in the compositions of the present invention should remain essentially unfilled (i.e. the cyclodextrin remains uncomplexed and free) or filled with only weakly complexing materials when in solution, in order to allow the cyclodextrin to absorb (i.e. complex with) various unwanted molecules, such as malodor molecules, when the composition is applied to a surface containing the unwanted molecules. Non-derivatized (normal) beta-cyclodextrin can be present at a level up to its solubility limit of about 1.85% (about 1.85 g in 100 grams of water) at room temperature. Beta-cyclodextrin is not preferred in compositions which call for a level of cyclodextrin higher than its water solubility limit. Non-derivatized beta-cyclodextrin is generally not preferred when the composition contains surfactant since it affects the surface activity of most of the preferred surfactants that are compatible with the derivatized cyclodextrins.

The level of low-degree of substitution cyclodextrin derivatives that are functionally-available in the present compositions is typically at least about 0.001%, preferably at least about 0.01%, and more preferably at least about 0.1%, by weight of the composition. The total level of cyclodextrin in the present composition will be at least equal to or greater than the level of functionally-available cyclodextrin. The level of functionally-available will typically be at least about 10%, preferably at least about 20%, and more preferably at least about 30%, by weight of the total level of cyclodextrin in the composition.

Concentrated compositions can also be used in order to deliver a less expensive product. When a concentrated product is used, i.e., when the total level of cyclodextrin used is from about 3% to about 60%, more preferably from about 5% to about 40%, by weight of the concentrated composition, it is preferable to dilute the concentrated composition before treating fabrics in order to avoid staining. Preferably the concentrated cyclodextrin composition is diluted with about 50% to about 6000%, more preferably with about 75% to about 2000%, most preferably with about 100% to about 1000% by weight of the concentrated composition of water. The resulting diluted compositions have usage concentrations of total cyclodextrin and functionally-available cyclodextrin as discussed hereinbefore, e.g., of from about 0.1% to about 5%, by weight of the diluted composition of total cyclodextrin and usage concentrations of functionally-available cyclodextrin of at least about 0.001%, by weight of the diluted composition.

B. Optional Ingredients

1. Carrier

The preferred carrier of the present invention is water. The water which is used can be distilled, deionized, or tap water. Water not only serves as the liquid carrier for the cyclodextrins, but it also facilitates the complexation reaction between the cyclodextrin molecules and any unwanted molecules on surfaces, such as malodorous molecules that are on inanimate surfaces such as fabric, when the surface is treated. It has been discovered that the intensity of unwanted malodorous molecules generated by some polar, low molecular weight organic amines, acids, and mercaptans is reduced when the malodor-contaminated surfaces are treated with an aqueous solution. Not to be bound by theory, it is believed that water solubilizes and depresses the vapor pressure of these polar, low molecular weight organic molecules, thus reducing their odor intensity.

The level of water in the present compositions can vary dependent upon the use of the composition. In compositions designed to be sprayed from manually or non-manually operated sprayers, the level of water is preferably high, from about 30% to about 99.9%, more preferably from about 50% to about 99.5%, and still more preferably from about 60% to about 95%.

Aqueous solutions that contain up to about 20% alcohol, preferably up to about 10% alcohol, and more preferably up to about 5% alcohol, are preferred for odor controlling compositions for treating fabrics. The dilute aqueous solution provides the maximum separation of cyclodextrin molecules on the fabric and thereby maximizes the chance that an odor molecule will interact with a cyclodextrin molecule.

2. Cyclodextrin-Compatible Surfactants

The stable compositions of the present invention for removing or reducing unwanted molecules preferably comprise cyclodextrin-compatible surfactants to form molecular aggregates with cyclodextrin-incompatible materials and to provide a low surface tension that permits the composition to spread more readily and more uniformly on hydrophobic surfaces, like polyester and nylon. The spreading of the composition also allows it to dry faster, so that the treated material is ready to use sooner. Furthermore, the composition containing a cyclodextrin-compatible surfactant can penetrate hydrophobic, oily soil better for improved reduction or removal of those types of unwanted molecules. For the stable compositions of the present invention comprising functionally-available cyclodextrin, the cyclodextrin-compatible surfactant facilitates the formation of micelles or vesicles with many cyclodextrin-incompatible materials (e.g. cyclodextrin-incompatible surfactants, cyclodextrin-incompatible enduring perfume materials, etc.), in order to preserve an effective amount of functionally-available cyclodextrin in the present compositions to reduce or remove unwanted molecules from the treated surfaces.

The surfactant for use in forming molecular aggregates with cyclodextrin-incompatible materials and in providing low surface tension in the composition of the present invention should be cyclodextrin-compatible, that is it should not substantially form a complex with the cyclodextrin so as to diminish performance of the cyclodextrin and/or the surfactant. Complex formation diminishes both the ability of the cyclodextrin to capture unwanted molecules, especially unwanted molecules, and the ability of the surfactant to lower the surface tension of the aqueous composition.

The important parameter in identifying cyclodextrin-compatible surfactants is its complexation constant with cyclodextrin, which is no greater than about 5,000 $M^{-1}$, preferably no greater than about 4,000 $M^{-1}$, and more preferably no greater than about 3,000 $M^{-1}$. Complexation constants can be measured according to the Test Method described hereinafter in Section IV.

Suitable cyclodextrin-compatible surfactants can also be readily identified by the absence of effect of cyclodextrin on the surface tension provided by the surfactant. This is achieved by determining the surface tension (in dyne/cm) of aqueous solutions of the surfactant in the presence and in the absence of about 1% of a specific cyclodextrin in the solutions. The aqueous solutions contain surfactant at concentrations of approximately 0.5%, 0.1%, 0.01%, and 0.005%. The cyclodextrin can affect the surface activity of a surfactant by elevating the surface tension of the surfactant solution. If the surface tension at a given concentration in water differs by more than about 10% from the surface tension of the same surfactant in the 1% solution of the cyclodextrin, that is an indication of a strong interaction between the surfactant and the cyclodextrin. The preferred surfactants herein should have a surface tension in an aqueous solution that is different (lower) by less than about 10%, preferably less than about 5%, and more preferably less than about 1% from that of the same concentration solution containing 1% cyclodextrin.

The cyclodextrin-compatible surfactants of the present invention are either weakly interactive with cyclodextrin (less than 5% elevation in surface tension), or non-interactive (less than 1% elevation in surface tension). Typical surfactants like sodium dodecyl sulfate and dodecanolpoly(6)ethoxylate, which are cyclodextrin-incompatible surfactants, are strongly interactive, with more than a 10% elevation in surface tension in the presence of a typical cyclodextrin like hydroxypropyl beta-cyclodextrin and methylated beta-cyclodextrin.

Typical levels of cyclodextrin-compatible surfactants in usage compositions are from about 0.01% to about 2%, preferably from about 0.03% to about 0.6%, more preferably from about 0.05% to about 0.3%, by weight of the composition. Typical levels of cyclodextrin-compatible surfactants in concentrated compositions are from about 0.1% to about 20%, preferably from about 0.2% to about 15%, more preferably from about 0.3% to about 10%, by weight of the concentrated composition.

Useful cyclodextrin-compatible surfactants in the present compositions include, but are not limited to, cyclodextrin-compatible surfactants selected from the group consisting of: block copolymer surfactant, siloxane surfactant, anionic surfactant, castor oil surfactant, sorbitan ester surfactant, polyethoxylated fatty alcohol surfactant, glycerol mono-fatty acid ester surfactant, polyethylene glycol fatty acid ester surfactant, fluorocarbon surfactant, and mixtures thereof. The cyclodextrin-compatible surfactants used in the present compositions are preferably selected from the group consisting of castor oil surfactant, sorbitan ester surfactant, polyethoxylated fatty alcohol surfactant, glycerol mono-fatty acid ester surfactant, polyethylene glycol fatty acid ester surfactant, fluorocarbon surfactant, and mixtures thereof.

a. Block Copolymer Surfactants

Nonlimiting examples of cyclodextrin-compatible nonionic surfactants include block copolymers of ethylene oxide and propylene oxide. Suitable block polyoxyethylene-polyoxypropylene polymeric surfactants, that are compatible with most cyclodextrins, include those based on ethylene glycol, propylene glycol, glycerol, trimethylolpropane and ethylenediamine as the initial reactive hydrogen compound. Polymeric compounds made from a sequential ethoxylation and propoxylation of initial compounds with a single reactive hydrogen atom, such as $C_{12-18}$ aliphatic alcohols, are not generally compatible with the cyclodextrin. Certain of the block polymer surfactant compounds designated Pluronic® and Tetronic® by the BASF-Wyandotte Corp., Wyandotte, Mich., are readily available.

Nonlimiting examples of cyclodextrin-compatible surfactants of this type include:

Pluronic Surfactants with the general formula H(EO)$_n$(PO)$_m$(EO)$_n$H,
wherein EO is an ethylene oxide group, PO is a propylene oxide group, and n and m are numbers that indicate the average number of the groups in the surfactants. Typical examples of cyclodextrin-compatible Pluronic surfactants are:

| Name | Average MW | Average n | Average m |
|---|---|---|---|
| L-101 | 3,800 | 4 | 59 |
| L-81 | 2,750 | 3 | 42 |
| L-44 | 2,200 | 10 | 23 |
| L-43 | 1,850 | 6 | 22 |
| F-38 | 4,700 | 43 | 16 |
| P-84 | 4,200 | 19 | 43, | and mixtures thereof.

Tetronic Surfactants with the general formula:

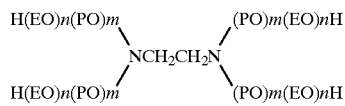

wherein EO, PO, n, and m have the same meanings as above. Typical examples of cyclodextrin-compatible Tetronic surfactants are:

| Name | Average MW | Average n | Average m |
|---|---|---|---|
| 901 | 4,700 | 3 | 18 |
| 908 | 25,000 | 114 | 22, | and mixtures thereof.

"Reverse" Pluronic and Tetronic surfactants have the following general formulas:

Reverse Pluronic Surfactants H(PO)$_m$(EO)$_n$(PO)$_m$H

Reverse Tetronic Surfactants

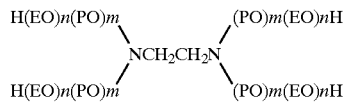

wherein EO, PO, n, and m have the same meanings as above. Typical examples of cyclodextrin-compatible Reverse Pluronic and Reverse Tetronic surfactants are:

Reverse Pluronic surfactants:

| Name | Average MW | Average n | Average m |
|---|---|---|---|
| 10 R5 | 1,950 | 8 | 22 |
| 25 R1 | 2,700 | 21 | 6 |

Reverse Tetronic surfactants

| Name | Average MW | Average n | Average m |
|---|---|---|---|
| 130 R2 | 7,740 | 9 | 26 |
| 70 R2 | 3,870 | 4 | 13 | and mixtures thereof.

b. Siloxane Surfactants

A preferred class of cyclodextrin-compatible nonionic surfactants are the polyalkyleneoxide polysiloxanes having a dimethyl polysiloxane hydrophobic moiety and one or more hydrophilic polyalkylene side chains and have the general formula:

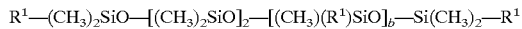

wherein a+b are from about 1 to about 50, preferably from about 3 to about 30, more preferably from about 10 to about 25, and each $R^1$ is the same or different and is selected from the group consisting of methyl and a poly(ethyleneoxide/propyleneoxide) copolymer group having the general formula:

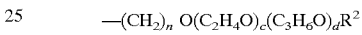

with at least one $R^1$ being a poly(ethyleneoxide/propyleneoxide) copolymer group, and wherein n is 3 or 4, preferably 3; total c (for all polyalkyleneoxy side groups) has a value of from 1 to about 100, preferably from about 6 to about 100; total d is from 0 to about 14, preferably from 0 to about 3; and more preferably d is 0; total c+d has a value of from about 5 to about 150, preferably from about 9 to about 100 and each $R^2$ is the same or different and is selected from the group consisting of hydrogen, an alkyl having 1 to 4 carbon atoms, and an acetyl group, preferably hydrogen and methyl group.

Examples of this type of surfactants are the Silwet® surfactants which are available OSi Specialties, Inc., Danbury, Conn. Representative Silwet surfactants are as follows.

| Name | Average MW | Average a + b | Average total c |
|---|---|---|---|
| L-7608 | 600 | 1 | 9 |
| L-7607 | 1,000 | 2 | 17 |
| L-77 | 600 | 1 | 9 |
| L-7605 | 6,000 | 20 | 99 |
| L-7604 | 4,000 | 21 | 53 |
| L-7600 | 4,000 | 11 | 68 |
| L-7657 | 5,000 | 20 | 76 |
| L-7602 | 3,000 | 20 | 29 |

The molecular weight of the polyalkyleneoxy group ($R^1$) is less than or equal to about 10,000. Preferably, the molecular weight of the polyalkyleneoxy group is less than or equal to about 8,000, and most preferably ranges from about 300 to about 5,000. Thus, the values of c and d can be those numbers which provide molecular weights within these ranges. However, the number of ethyleneoxy units (—C$_2$H$_4$O) in the polyether chain ($R^1$) must be sufficient to render the polyalkyleneoxide polysiloxane water dispersible or water soluble. If propyleneoxy groups are present in the polyalkylenoxy chain, they can be distributed randomly in the chain or exist as blocks. Preferred Silwet surfactants are L-7600, L-7602, L-7604, L-7605, L-7657, and mixtures thereof. Besides surface activity, polyalkyleneoxide polysiloxane surfactants can also provide other benefits, such as antistatic benefits, lubricity and softness to fabrics.

The preparation of polyalkyleneoxide polysiloxanes is well known in the art. Polyalkyleneoxide polysiloxanes of the present invention can be prepared according to the procedure set forth in U.S. Pat. No. 3,299,112, incorporated herein by reference. Typically, polyalkyleneoxide polysiloxanes of the surfactant blend of the present invention are readily prepared by an addition reaction between a hydrosiloxane (i.e., a siloxane containing silicon-bonded hydrogen) and an alkenyl ether (e.g., a vinyl, allyl, or methallyl ether) of an alkoxy or hydroxy end-blocked polyalkylene oxide). The reaction conditions employed in addition reactions of this type are well known in the art and in general involve heating the reactants (e.g., at a temperature of from about 85° C. to 110° C.) in the presence of a platinum catalyst (e.g., chloroplatinic acid) and a solvent (e.g., toluene).

c. Anionic Surfactants

Nonlimiting examples of cyclodextrin-compatible anionic surfactants are the alkyldiphenyl oxide disulfonate, having the general formula:

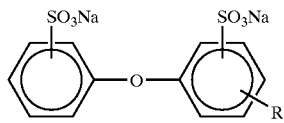

wherein R is an alkyl group. Examples of this type of surfactants are available from the Dow Chemical Company under the trade name Dowfax® wherein R is a linear or branched $C_6$–$C_{16}$ alkyl group. An example of these cyclodextrin-compatible anionic surfactant is Dowfax 3B2 with R being approximately a linear $C_{10}$ group. These anionic surfactants are preferably not used when an antimicrobial active or preservative is used which is cationic to minimize the interaction with the cationic actives, since the effect of both surfactant and active would be diminished.

d. Castor Oil Surfactants

The cyclodextrin-compatible surfactants useful in the present invention to Form molecular aggregates, such as micelles or vesicles, with the cyclodextrin-incompatible materials of the present invention further include polyoxyethylene castor oil ethers or polyoxyethylene hardened castor oil ethers or mixtures thereof, which are either partially or fully hydrogenated. These ethoxylates have the following general formulae:

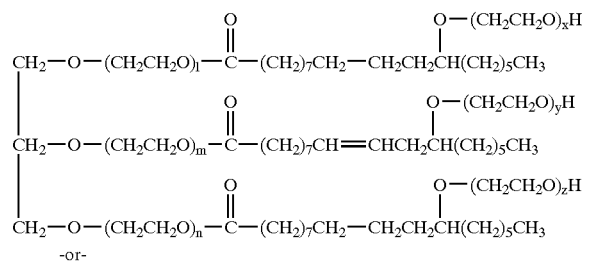

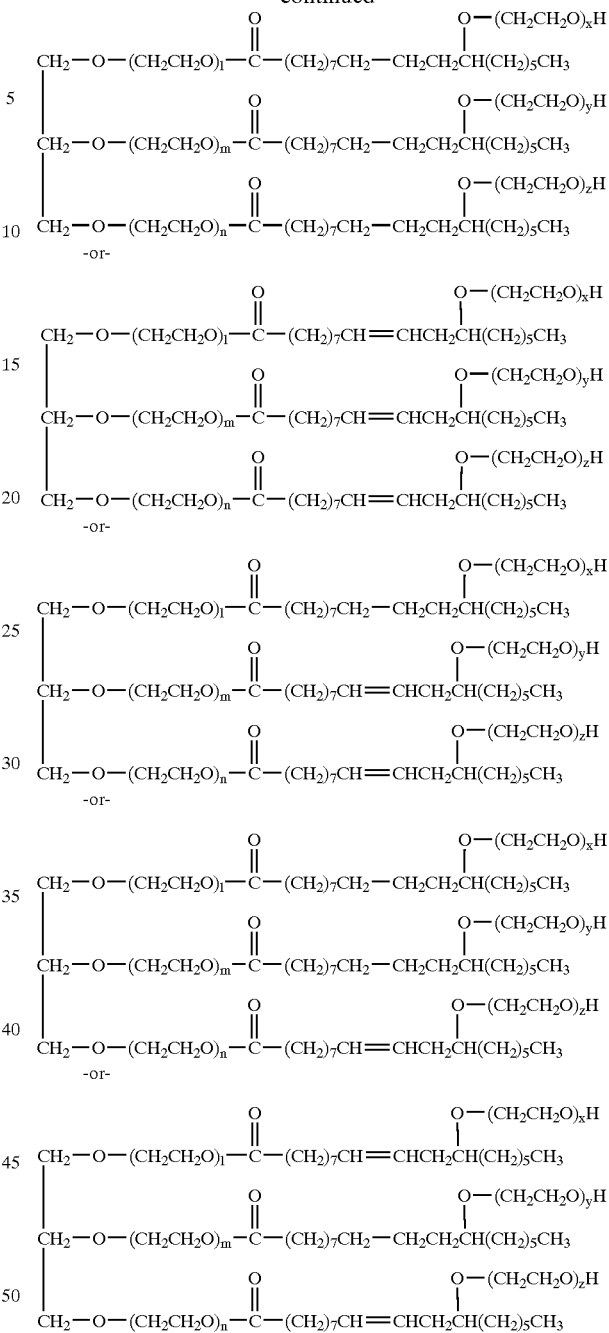

These ethoxylates can be used alone or in any mixture thereof. The average ethylene oxide addition mole number (i.e., l+m+n+x+y+z in the above formula) of these ethoxylates is generally from about 7 to about 100, and preferably from about 20 to about 80. Castor oil surfactants are commerically available from Nikko under the trade names HCO 40 and HCO 60 and from BASF under the trade names Cremphor™ RH 40, RH 60, and CO 60.

e. Sorbitan Ester Surfactants

The sorbitan esters of long-chain fatty acids usable as cyclodextrin-compatible surfactants to form molecular aggregates with cyclodextrin-incompatible materials of the present invention include those having long-chain fatty acid residues with 14 to 18 carbon atoms, desirably 16 to 18 carbon atoms. Furthermore, the esterification degree of the sorbitan polyesters of long-chain fatty acids is desirably 2.5 to 3.5, especially 2.8 to 3.2. Typical examples of these sorbitan polyesters of long-chain fatty acids are sorbitan tripalmitate, sorbitan trioleate, and sorbitan tallow fatty acid triesters.

Other suitable sorbitan ester surfactants include sorbitan fatty acid esters, particularly the mono-and tri-esters of the formula:

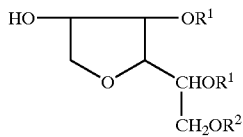

wherein $R^1$ is H or

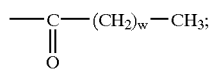

and $R^2$ is

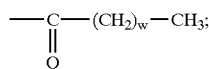

and w is from about 10 to about 16.

Further suitable sorbitan ester surfactants include polyethoxylated sorbitan fatty acid esters, particularly those of the formula:

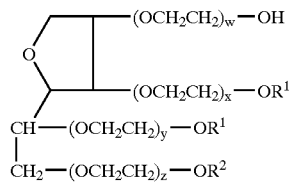

wherein $R^1$ is H or

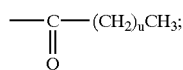

and $R^2$ is

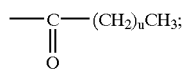

u is from about 10 to about 16 and average (w+x+y+z) is from about 2 to about 20. Preferably, u is 16 and average (w+x+y+z) is from about 2 to about 4.

f. Polyethoxylated Fatty Alcohol Surfactants

Cyclodextrin-compatible surfactants further include polyethoxylated fatty alcohol surfactants having the formula:

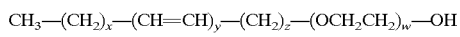

wherein w is from about 0 to about 100, preferably from about 0 to about 80; y is 0 or 1; x is from about 1 to about 10; z is from about 1 to about 10; x+z+y=11 to 25, preferably 11 to 23.

Branched (polyethoxylated) fatty alcohols having the following formula are also suitable as cyclodextrin-compatible surfactants in the present compositions:

wherein R is a branched alkyl group of from about 10 to about 26 carbon atoms and w is as specified above.

g. Glycerol Mono-Fatty Acid Ester Surfactants

Further cyclodextrin-compatible surfactants include glycerol mono-fatty acid esters, particularly glycerol monostearate, oleate, palmitate or laurate.

h. Polyethylene Glycol Fatty Acid Ester Surfactants

Fatty acid esters of polyethylene glycol, particularly those of the following formula, are cyclodextrin-compatible surfactants useful herein:

-or-

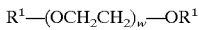

wherein $R^1$ is a stearoyl, lauroyl, oleoyl or palmitoyl residue; w is from about 2 to about 20, preferably from about 2 to about 8.

i. Fluorocarbon Surfactants

Further cyclodextrin-compatible surfactants useful in the present compositions include fluorocarbon surfactants. Fluorocarbon surfactants are a class of surfactants wherein the hydrophobic part of the amphiphile comprises at least in part some portion of a carbon-based linear or cyclic moiety having fluorines attached to the carbon where typically hydrogens would be attached to the carbons together with a hydrophilic head group. Some typical nonlimiting fluorocarbon surfactants include fluorinated alkyl polyoxyalkylene, and fluorinated alkyl esters as well as ionic surfactants. Representative structures for these compounds are given below:

 (1)

 (2)

 (3)

 (4)

wherein $R_f$ contains from about 6 to about 18 carbons each having from about 0 to about 3 fluorines attached. R is either an alkyl or alkylene oxide group which, when present, has from about 1 to about 10 carbons and $R_1$ represents an alkylene radical having from about 1 to about 4 w carbons. $R_2$ is either a hydrogen or a small alkyl capping group having from about 1 to about 3 carbons. $R_3$ represents a hydrocarbon moiety comprising from about 2 to about 22 including the carbon on the ester group. This hydrocarbon can be linear, branched or cyclic saturated or unsaturated and contained moieties based on oxygen, nitrogen, and sulfur including, but not limited to ethers, alcohols, esters, carboxylates, amides, amines, thio-esters, and thiols; these oxygen, nitrogen, and sulfur moieties can either interrupt the hydrocarbon chain or be pendant on the hydrocarbon chain. In structure 3, Y represents a hydrocarbon group that can be an alkyl, pyridine group, amidopropyl, etc. that acts as a linking group between the fluorinated chain and the hydrophilic head group. In structures 3 and 4, Z represents a cationic, anionic, and amphoteric hydrophilic head groups including, but not limited to carboxylates, sulfates, sulfonates, quaternary ammonium groups, and betaines.

Nonlimiting commercially available examples of these structures include Zonyl® 9075, FSO, FSN, FS-300, FS-310, FSN-100, FSO-100, FTS, TBC from DuPont and Fluorad™ surfactants FC-430, FC-431, FC-740, FC-99, FC-120. FC-754, FC170C, and FC-171 from the 3M™ company in St. Paul, Minn.

3. Water-Soluble Polymers

Some water-soluble polymers, e.g., water-soluble cationic polymer and water-soluble anionic polymers can be used in the composition of the present invention to provide additional odor control benefits.

a. Cationic polymers. e.g. Polyamines

Water-soluble cationic polymers, e.g., those containing amino functionalities, amido functionalities, and mixtures thereof, are useful in the present invention to control certain acid-type odors.

b. Anionic Polymers. e.g. Polyacrylic Acid

Water-soluble anionic polymers, e.g., polyacrylic acids and their water-soluble salts are useful in the present invention to control certain amine-type odors. Preferred polyacrylic acids and their alkali metal salts have an average molecular weight of less than about 20,000, more preferably less than 5,000. Polymers containing sulfonic acid groups, phosphoric acid groups, phosphonic acid groups, and their water-soluble salts, and mixtures thereof, and mixtures with carboxylic acid and carboxylate groups, are also suitable.

Water-soluble polymers containing both cationic and anionic functionalities are also suitable. Examples of these polymers are given in U.S. Pat. No. 4,909,986, issued Mar. 20, 1990 to N. Kobayashi and A. Kawazoe, incorporated herein by reference. Another example of water-soluble polymers containing both cationic and anionic functionalities is a copolymer of dimethyldiallyl ammonium chloride and acrylic acid, commercially available under the trade name Merquat 280® from Calgon.

When a water-soluble polymer is used it is typically present at a level of from about 0.001% to about 3%, preferably from about 0.005% to about 2%, more preferably from about 0.01% to about 1%, and even more preferably from about 0.05% to about 0.5%, by weight of the usage composition.

4. Wrinkle Control Agents

The present compositions can optionally further comprise a wrinkle control agent, wherein the wrinkle control agent is preferably cyclodextrin-compatible. Cyclodextrin-compatible wrinkle control agents useful herein include fiber lubricant, shape retention polymer, hydrophilic plasticizer, lithium salt, and mixtures thereof. Such cyclodextrin-compatible wrinkle control agents are described in detail in U.S. Pat. No. 6,001,343 issued Dec. 14, 1999 to Trinh et al., which is hereby incorporated by reference herein. Wrinkle control compositions that can be suitable as base compositions of the present invention that contain low-degree of substitution cyclodextrin-derivatives, especially compositions that can be used in a cabinet-type or bag-type apparatus for conditioning garments, are also disclosed in International Application No. PCT/US98/08129, filed Apr. 27, 1998, and published Nov. 4, 1999 as WO99/55950 by Hubesch et al. (P&G Case CM-1714); and International Application No. PCT/US98/08124, filed Apr. 27, 1998, and published Nov. 4, 1999 as WO99/55816 by Woo et al. (P&G Case 7097) which are incorporated herein by reference.

5. Cyclodextrin-Incompatible Surfactants

Cyclodextrin-incompatible surfactants have a strong affinity for complexing with cyclodextrin, which has traditionally made it difficult to formulate compositions containing both functionally-available cyclodextrin and cyclodextrin-incompatible materials. Cyclodextrin-incompatible surfactants typically have a complexation constant of greater than about 5,000 $M^{-1}$, preferably greater than about 8,000 $M^{-1}$, and more preferably greater than about 10,000 $M^-$. However, Applicants have surprisingly found that compositions can be carefully formulated, as described herein, to comprise both cyclodextrin-incompatible materials and functionally-available cyclodextrin.

Cyclodextrin-incompatible surfactants generally can be readily identified by the noticeable effect of cyclodextrin on the surface tension provided by the cyclodextrin-incompatible surfactant. This is achieved by determining the surface tension (in dyne/cm) of aqueous solutions of the cyclodextrin-incompatible surfactant in the presence and in the absence of about 1% of a specific cyclodextrin in the solutions. The aqueous solutions contain cyclodextrin-incompatible surfactant at concentrations of approximately 0.5%, 0.1%, 0.01%, and 0.005%. The cyclodextrin can affect the surface activity of a surfactant by elevating the surface tension of the surfactant solution. If the surface tension at a given concentration in water differs by more than about 10% from the surface tension of the same surfactant in the 1% solution of the cyclodextrin, that is an indication of a strong interaction between the surfactant and the cyclodextrin, and identifies the surfactant as a cyclodextrin-incompatible surfactant. The cyclodextrin-incompatible surfactants herein typically have a surface tension in an aqueous solution that is different (lower) by at least about 10%, preferably at least about 13%, and more preferably at least about 15% from that of the same concentration solution containing 1% cyclodextrin.

When the cyclodextrin-incompatible surfactant is combined with other components (e.g. cyclodextrin-compatible surfactants) of the present compositions, before the addition of the cyclodextrin to form the present compositions, the cyclodextrin-incompatible surfactant is maintained in molecular aggregates such as micelles or vesicles in the composition matrix. The cyclodextrin-incompatible surfactants of the present invention generally have a critical micelle concentration ("CMC") of at least about 104 mol/l, preferably at least about $10^{-3}$ mol/l. When combined with other surfactants, such as cyclodextrin-compatible surfactants (as described hereinafter) having a complexation constant of no greater than about 5,000 $M^{-1}$, preferably no greater than about 4,000 $M^{-1}$, and more preferably no greater than about 3,000 $M^{-1}$, the total CMC of the surfactant mixture of the present compositions is no greater than about $10^{-2}$ mol/l, preferably no greater than about $10^{-3}$ mol/l, and more preferably no greater than about $10^{-4}$ mol/l.

Examples of cyclodextrin-incompatible surfactants include anionic surfactants, amphoteric surfactants, cationic surfactants, and mixtures thereof. Such surfactants are commonly used in detergent compositions, fabric softening compositions, shampoo compositions, hard surface cleaning compositions, cosmetic compositions, personal care compositions/bars, mouth rinse compositions, body wash compositions, shaving compositions, skin moisturizing compositions, and the like.

a. Anionic Surfactants

Anionic surfactants that tend to be cyclodextrin-incompatible and are useful herein include alkyl and alkyl ether sulfates. These materials have the respective formulae $ROSO_3M$ and $RO(C_2H_4O)_xSO_3M$, wherein R is alkyl or alkenyl of from about 8 to about 30 carbon atoms, x is 1 to about 10, and M is hydrogen or a cation such as ammonium, alkanolammonium (e.g., triethanolammonium), a monovalent metal cation (e.g., sodium and potassium), or a polyvalent metal cation (e.g., magnesium and calcium). Preferably, M should be chosen such that the anionic surfactant component is water soluble. The anionic surfactant or surfactants should be chosen such that the Krafft temperature is about 15° C. or less, preferably about 10° C. or less, and more preferably about 0° C. or less. It is also preferred that the anionic surfactant be soluble in the composition hereof.

Krafft temperature refers to the point at which solubility of an ionic surfactant becomes determined by crystal lattice energy and heat of hydration, and corresponds to a point at which solubility undergoes a sharp, discontinuous increase with increasing temperature. Each type of surfactant will have its own characteristic Krafft temperature. Krafft temperature for ionic surfactants is, in general, well known and understood in the art. See, for example, Myers, D., *Surfactant Science and Technology*, pp. 82–85, VCH Publishers, Inc. (New York, N.Y., USA), 1988 (ISBN 0-89573-399-0), which is incorporated by reference herein in its entirety.

In the alkyl and alkyl ether sulfates described above, R can have from about 12 to about 18 carbon atoms in both the alkyl and alkyl ether sulfates. The alkyl ether sulfates are typically made as condensation products of ethylene oxide and monohydric alcohols having from about 8 to about 24 carbon atoms. The alcohols can be derived from fats, e.g., coconut oil, palm oil, tallow, or the like, or the alcohols can be synthetic. Lauryl alcohol and straight chain alcohols derived from coconut oil and palm oil are useful herein. Such alcohols are reacted with 1 to about 10, and especially about 3, molar proportions of ethylene oxide and the resulting mixture of molecular species having, for example, an average of 3 moles of ethylene oxide per mole of alcohol, is sulfated and neutralized.

Specific examples of alkyl ether sulfates which can be used in the present invention as cyclodextrin-incompatible surfactants are sodium and ammonium salts of coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from 1 to about 4 moles of ethylene oxide. Such a mixture also comprises from 0% to about 20% by weight $C_{12-13}$ compounds; from about 60% to about 100% by weight of $C_{14-16}$ compounds, from 0% to about 20% by weight of $C_{17-19}$ compounds; from about 3% to about 30% by weight of compounds having a degree of ethoxylation of 0; from about 45% to about 90% by weight of compounds having a degree of ethoxylation of from 1 to about 4; from about 10% to about 25% by weight of compounds having a degree of ethoxylation of from about 4 to about 8; and from about 0.1% to about 15% by weight of compounds having a degree of ethoxylation greater than about 8.

Other anionic surfactants that tend to be cyclodextrin-incompatible are the water-soluble salts of organic, sulfuric acid reaction products of the general formula $[R_1-SO_3-M]$ where $R_1$ is selected from the group consisting of a straight or branched chain, saturated aliphatic hydrocarbon radical having from about 8 to about 24, preferably about 10 to about 18, carbon atoms; and M is as previously described above in this section. Examples of such surfactants are the salts of an organic sulfuric acid reaction product of a hydrocarbon of the methane series, including iso-, neo-, and n-paraffins, having about 8 to about 24 carbon atoms, preferably about 12 to about 18 carbon atoms and a sulfonating agent, e.g., $SO_3$, $H_2SO_4$, obtained according to known sulfonation methods, including bleaching and hydrolysis. Preferred are alkali metal and ammonium sulfonated $C_{10-18}$ n-paraffins.

Still other anionic surfactants that tend to be cyclodextrin-incompatible are the reaction products of fatty acids esterified with isethionic acid and neutralized with sodium hydroxide where, for example, the fatty acids are derived from coconut or palm oil; or sodium or potassium salts of fatty acid amides of methyl tauride in which the fatty acids, for example, are derived from coconut oil. Other similar anionic surfactants are described in U.S. Pat. Nos. 2,486,921, 2,486,922, and 2,396,278, which are incorporated by reference herein in their entirety.

Still other useful anionic surfactants that tend to be cyclodextrin-incompatible are those that are derived from taurine, which is also known as 2-aminoethanesulfonic acid. An example of such an acid is N-acyl-N-methyl taurate.

Other anionic surfactants that tend to be cyclodextrin-incompatible and are suitable for use in the present compositions are the succinates, examples of which include disodium N-octadecylsulfosuccinate; disodium lauryl sulfosuccinate; diammonium lauryl sulfosuccinate; tetrasodium N-(1,2-dicarboxyethyl)-N-octadecylsulfosuccinate; the diamyl ester of sodium sulfosuccinic acid; the dihexyl ester of sodium sulfosuccinic acid; and the dioctyl ester of sodium sulfosuccinic acid.

Other suitable anionic surfactants include olefin sulfonates having about 10 to about 24 carbon atoms. The term "olefin sulfonates" is used herein to mean compounds which can be produced by the suffonation of alpha-olefins by means of uncomplexed sulfur trioxide, followed by neutralization of the acid reaction mixture in conditions such that any sulfones which have been formed in the reaction are hydrolyzed to give the corresponding hydroxyalkane-sulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The alpha-olefins from which the olefin sulfonates are derived are mono-olefins having about 12 to about 24 carbon atoms, preferably about 14 to about 16 carbon atoms. Preferably, they are straight chain olefins.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A specific alpha-olefin sulfonate mixture of the above type is described more fully in U.S. Pat. No. 3,332,880, to Pflaumer and Kessler, issued Jul. 25, 1967, which is incorporated by reference herein in its entirety.

Another class of anionic surfactants that tend to be cyclodextrin-incompatible and are suitable for use in the present compositions are the beta-alkyloxy alkane sulfonates. These compounds have the following formula:

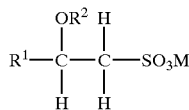

where $R^1$ is a straight chain alkyl group having from about 6 to about 20 carbon atoms, $R^2$ is a lower allyl group having from about 1, preferred, to about 3 carbon atoms, and M is as hereinbefore described.

Many other anionic surfactants that tend to be cyclodextrin-incompatible and are suitable for use in the present compositions are described in McCutcheon's, Emulsifiers and Detergents, 1989 Annual, published by M. C. Publishing Co., and in U.S. Pat. No. 3,929,678, which descriptions are incorporated herein by reference in their entirety.

Examples of anionic surfactants that tend to be cyclodextrin-incompatible and useful in detergent compositions and/or shampoo compositions herein include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium N-lauroyl-N-methyl taurate, sodium tridecyl benzene sulfonate, and sodium dodecyl benzene sulfonate. Preferred for use herein are detersive anionic surfactants selected from the group consisting of ammonium laureth-3 sulfate, sodium alureth-3 sulfate, ammonium lauryl sulfate, sodium lauryl sulfate, and mixtures thereof.

b. Amphoteric Surfactants

The cyclodextrin-incompatible surfactants of the present invention can also include amphoteric surfactants. The term "amphoteric surfactant," as used herein, is also intended to encompass zwitterionic surfactants, which are well known to formulators skilled in the art as a subset of amphoteric surfactants. A wide variety of amphoteric surfactants tend to be cyclodextrin-incompatible, and can be incorporated in the compositions of the present invention containing functionally-available cyclodextrin. Particularly useful amphoteric surfactants are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Nonlimiting examples of amphoteric surfactants that tend to be cyclodextrin-incompatible and are useful in the compositions of the present invention are disclosed in McCutcheon's, Detergents and Emulsifiers, North American edition (1986), published by allured Publishing Corporation; and McCutcheon's, Functional Materials, North American Edition (1992); both of which are incorporated by reference herein in their entirety.

Examples of amphoteric or zwitterionic surfactants include the betaines, sultaines, and hydroxysultaines. Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl c betaine, stearyl bis-(2-hydroxypropyl) carboxymethyl betaine, oleyl d-methyl gamma-carboxypropyl betaine, lauryl bis-(2-hydroxypropyl)alpha-carboxyethyl betaine, coco dimethyl sulfopropyl betaine, stearyl dimethyl sulfopropyl betaine, stearyl betaine, lauryl dimethyl sulfoethyl betaine, lauryl bis-(2-hydroxyethyl) sulfopropyl betaine, and amidobetaines and amidosulfobetaines (wherein the RCONH $(CH_2)_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Examples of sultaines and hydroxysultaines include materials such as cocamidopropyl hydroxysultaine (available as Mirataine CBS from Rhone Poulenc).

Suitable amphoteric surfactants that tend to be cyclodextrin-incompatible have the following structure:

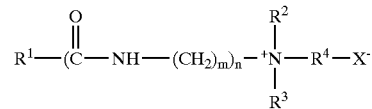

wherein $R^1$ is unsubstituted, saturated or unsaturated, straight or branched chain alkyl having from about 9 to about 22 carbon atoms. Preferred $R^1$ has from about 11 to about 18 carbon atoms; more preferably from about 12 to about 18 carbon atoms; more preferably still from about 14 to about 18 carbon atoms; m is an integer from 1 to about 3, more preferably from about 2 to about 3, and more preferably about 3; n is either 0 or 1, preferably 1; $R^2$ and $R^3$ are independently selected from the group consisting of alkyl having from 1 to about 3 carbon atoms, unsubstituted or mono-substituted with hydroxy, preferred $R^2$ and $R^3$ are $CH_3$; X is selected from the group consisting of $CO_2$, $SO_3$ and $SO_4$; $R^4$ is selected from the group consisting of saturated or unsaturated, straight or branched chain allyl, unsubstituted or monosubstituted with hydroxy, having from 1 to about 5 carbon atoms. When X is $CO_2$, $R^4$ preferably has 1 or 3 carbon atoms, more preferably 1 carbon atom. When X is $SO_3$ or $SO_4$, $R^4$ preferably has from about 2 to about 4 carbon atoms, more preferably 3 carbon atoms.

Examples of amphoteric surfactants of the present invention include the following compounds: cetyl dimethyl betaine; cocamidopropylbetaine (wherein the alkyl group has from about 9 to about 13 carbon atoms); cocamidopropyl hydroxy sultaine (wherein the alkyl group has from about 9 to about 13 carbon atoms); stearyl dimethyl betaine; and behenyl dimethyl betaine.

Other amphoteric surfactants of the present invention that tend to be cyclodextrin-incompatible include cetyl dimethyl betaine, cocamidopropyl betaine, stearyl dimethyl betaine, and cocamidopropyl hydroxy sultaine.

Examples of other useful amphoteric surfactants that tend to be cyclodextrin-incompatible are alkyliminoacetates, and iminodialkanoates and aminoalkanoates of the formulas $RN[(CH_2)_mCO_2M]_2$ and $RNH(CH_2)_mCO_2M$ wherein m is from 1 to 4, R is a $C_8–C_{22}$ alkyl or alkenyl, and M is H, alkali metal, alkaline earth metal ammonium, or alkanolammonium. Also included are imidazolinium and ammonium derivatives. Other examples of useful amphoterics include phosphates, such as cocamidopropyl PG-dimonium chloride phosphate (commercially available as Monaquat PTC, from Mona Corp.).

The cyclodextrin-incompatible surfactant of the compositions of the present invention can also include amino acid derivative surfactants. By amino acid derivative, as defined herein, is meant a surfactant that has the basic chemical structure of an amino acid compound, i.e. that contains a structural component of one of the naturally-occurring amino acids. Common amino acids from which such surfactants are derived include glycine, N-methyl glycine which is also known as sarcosine, glutamic acid, arginine, alanine, phenylalanine, and the like. Other surfactants suitable for use in the present compositions are those that are derived from amino acids. Also useful herein are salts of these amino acid derived surfactants. Nonlimiting examples of such surfactants include N-acyl-L-glutamate; N-acyl-N-methyl-α-alanate; N-acylsarcosinate; N-alkylaminopropionates and N-alkyliminodipropionates specific examples of which include N-lauryl-β-amino propionic acid or salts thereof, and N-lauryl-β-imino-dipropionic acid; sodium lauryl sarcosinate, sodium lauroyl sarcosinate, lauryl sarcosine, cocoyl sarcosine, and mixtures thereof.

c. Cationic Surfactants

Cationic surfactants typically contain quaternary nitrogen moieties and tend to be cyclodextrin-incompatible. Cationic surfactants among those useful herein are disclosed in the following documents, all of which are incorporated by reference herein in their entirety: M. C. Publishing Co., McCutcheon's, Detergents & Emulsifiers, (North American edition 1979); Schwartz, et al., Surface Active Agents, Their Chemistry and Technology, New York: Interscience Publishers, 1949; U.S. Pat. No. 3,155,591, Hilfer, issued Nov. 3, 1964; U.S. Pat. No. 3,929,678, Laughlin et al., issued Dec. 30, 1975; U.S. Pat. No. 3,959,461, Bailey et al., issued May 25, 1976; and U.S. Pat. No. 4,387,090, Bolich, Jr., issued Jun. 7, 1983.

Among the cationic surfactant materials that tend to be cyclodextrin-incompatible and are useful herein are those corresponding to the general formula:

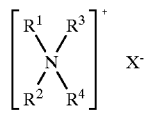

wherein $R^1$, $R^2$, $R^3$, and $R^4$ are independently selected from an aliphatic group of from 1 to about 22 carbon atoms or an aromatic, alkoxy, polyoxyalkylene, alkylamido, hydroxyalkyl, aryl or alkylaryl group having up to about 22 carbon atoms; and X is a salt-forming anion such as those selected from halogen, (e.g. chloride, bromide), acetate, citrate, lactate, glycolate, phosphate nitrate, sulfate, and alkylsulfate radicals. The aliphatic groups can contain, in addition to carbon and hydrogen atoms, ether linkages, and other groups such as amino groups. The longer chain aliphatic groups, e.g., those of about 12 carbons, or higher, can be saturated or unsaturated. Preferred is when $R^1$, $R^2$, $R^3$, and $R^4$ are independently selected from C, to about $C_{22}$ alkyl. Especially preferred are cationic materials containing two long alkyl chains and two short alkyl chains or those containing one long alkyl chain and three short alkyl chains. The long alkyl chains in the compounds described in the previous sentence have from about 12 to about 22 carbon atoms, preferably from about 16 to about 22 carbon atoms, and the short alkyl chains in the compounds described in the previous sentence have from 1 to about 3 carbon atoms, preferably from 1 to about 2 carbon atoms.

Also preferred are cationic materials in which at least one of the substituents is selected from hydroxyalkyl, preferably hydroxyethyl or hydroxy propyl, or polyoxyalkylene, preferably polyoxyethylene or polyoxypropylene wherein the total degree of ethoxylation or propoxylation in the molecule is from about 5 to about 20. Nonlimiting examples of commercially available materials include Variquat K1215 and 638 from Witco Chemical, Dehyquat SP from Henkel, and Atlas G265 from ICI Americas.

Other cationic materials that tend to be cyclodextrin-incompatible include the materials having the following CTFA designations: quaternium-8, quaternium-24, quaternium-26, quaternium-27, quaternium-30, quaternium-33, quaternium-43, quaternium-52, quaternium-53, quaternium-56, quaternium-60, quaternium-62, quaternium-70, quaternium-72, quaternium-75, quaternium-77, quaternium-78, quaternium-79, quaternium-80, quaternium-81, quaternium-82, quaternium-83, quaternium-84, and mixtures thereof.

Salts of primary, secondary and tertiary fatty amines are also suitable cationic surfactant materials. The alkyl groups of such amines preferably have from about 12 to about 22 carbon atoms, and can be substituted or unsubstituted. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (with 5 moles of ethylene oxide) stearylamine, dihydroxy ethyl stearylamine, and arachidylbehenylamine. Suitable amine salts include the halogen, acetate, phosphate, nitrate, citrate, lactate, and alkyl sulfate salts. Such salts include stearylamine hydrochloride, soyamine chloride, stearylamine formate, N-tallowpropane diamine dichloride and stearamidopropyl dimethylamine citrate. Cationic amine surfactants included among those useful in the present invention are disclosed in U.S. Pat. No. 4,275,055, Nachtigal, et al., issued Jun. 23, 1981, which is incorporated by reference herein in its entirety.

The following Table provides non-limiting examples of cyclodextrin-incompatible surfactants of the present invention, along with their respective complexation constants with cyclodextrin.

Examples Of Cyclodextrin-Incompatible Surfactants

| CD incompatible surfactant | Complexation Constant (K) |
| --- | --- |
| Sodium dodecyl sulfate | about 22000 |
| Sodium laurate | about 16000 |
| Lauramine oxide | about 7500 |
| Dodecyltrimethylammonium bromide | about 18100 |
| Cetyl pyridinium chloride | about 48000 |
| Laureth-6 | about 10000 |

6. Cyclodextrin-Incompatible Perfume Materials

The stable compositions of the present invention preferably provide a "scent signal" in the form of a pleasant odor which imparts a freshness impression to the treated surface and can serve as a signal of the capturing of the unwanted molecules, e.g. malodorous molecules, from the treated surfaces, such as fabrics. The cyclodextrin-incompatible perfume materials herein are designed to provide, at least in part, a lasting perfume scent. Perfume is added at levels of from about 0% to about 3%, preferably from about 0.003% to about 2%, more preferably from about 0.005% to about 1%, by weight of the usage composition.

Perfume can be added to provide a more lasting odor on the treated surfaces. When stronger levels of perfume are preferred, relatively higher levels of perfume can be added. Any type of perfume can be incorporated into the compositions of the present invention so long as the enduring hydrophobic perfume materials that are cyclodextrin-incompatible are properly incorporated in the present compositions such that functionally-available cyclodextrin remains in the compositions at the requisite levels. The perfume ingredients can be either hydrophilic or hydrophobic. The cyclodextrin-incompatible perfume materials of the present invention have complexation constants with cyclodextrin of greater than about 5,000 $M^{-1}$, preferably greater than about 8,000 $M^{-1}$, and more preferably greater than about 10,000 $M^{-1}$.

In order to provide long lasting effects, the perfume is at least partially hydrophobic and has a relatively high boiling point. I.e., the perfume is composed predominantly of perfume materials selected from two groups of ingredients, namely, (a) hydrophobic ingredients (i.e. generally cyclodextrin-incompatible perfume materials) having a ClogP of more than about 3, more preferably more than about 3.5, and (b) ingredients having a molecular weight above about 210, preferably above about 220. Typically, at least about 50%, preferably at least about 60%, more preferably at least about 70%, and most preferably at least about 80% by weight of the perfume is composed of cyclodextrin-incompatible enduring perfume materials of the above groups (a) and (b). For these preferred perfumes, the total cyclodextrin to perfume weight ratio is typically of from about 2:1 to about 200:1; preferably from about 4:1 to about 100:1, more preferably from about 6:1 to about 50:1, and even more preferably from about 8:1 to about 30:1.

Hydrophobic perfume materials have a tendency to strongly complex with the cyclodextrins, thus being cyclodextrin-incompatible. The degree of hydrophobicity of a perfume ingredient can be correlated with its octanol/water partition coefficient P. The octanol/water partition coefficient of a perfume ingredient is the ratio between its equilibrium concentration in octanol and in water. A perfume ingredient with a greater partition coefficient P is considered to be more hydrophobic. Conversely, a perfume ingredient with a smaller partition coefficient P is considered to be more hydrophilic. Since the partition coefficients of the perfume ingredients normally have high values, they are more conveniently given in the form of their logarithm to the base 10, logP. Thus the cyclodextrin-incompatible enduring perfume materials of this invention have logP of about 3 or higher, preferably of about 3.5 or higher.

The logP of many perfume ingredients have been reported in; for example, the Pomona92 database, available from Daylight Chemical Information Systems, Inc. (Daylight CIS), Irvine, Calif., contains many, along with citations to the original literature. However, the logP values are most conveniently calculated by the "CLOGP" program, also available from Daylight CIS. This program also lists experimental logP values when they are available in the Pomona92 database. The "calculated logP" (ClogP) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990, incorporated herein by reference). The fragment approach is based on the chemical structure of each perfume ingredient, and takes into account the numbers and types of atoms, the atom connectivity, and chemical bonding. The ClogP values, which are the most reliable and widely used estimates for this physicochemical property, are used instead of the experimental logP values in the selection of perfume ingredients which are useful in the present invention.

Non-limiting examples of the cyclodextrin-incompatible enduring (hydrophobic) perfume materials are selected from the group consisting of: diethyl phthalate, methyl dihydro jasmonate, lyral, hexyl salicylate, iso-E super, hexyl cinnamic aldehyde, iso-propyl myristate, galaxolide, phenyl-ethyl-phenyl acetate, cis-jasmone; dimethyl benzyl carbinyl acetate; ethyl vanillin; geranyl acetate; alpha-ionone; beta-ionone; gamma-ionone; lauric aldehyde; methyl dihydrojasmonate; methyl nonyl acetaldehyde; gamma-nonalactone; phenoxy ethyl iso-butyrate; phenyl ethyl dimethyl carbinol; phenyl ethyl dimethyl carbinyl acetate; alpha-methyl-4-(2-methylpropyl)-benzenepropanal (Suzaral T); 6-acetyl-1,1,3, 4,4,6-hexamethyl tetrahydronaphthalene (Tonalid); undecylenic aldehyde; vanillin; 2,5,5-trimethyl-2-pentyl-cyclopentanone (veloutone); 2-tert-butylcyclohexanol (verdol); verdox; para-tert-butylcyclohexyl acetate (vertenex); and mixtures thereof. Enduring perfume compositions can be formulated using these cyclodextrin-incompatible enduring perfume materials, preferably at a level of at least about 5%, more preferably at least about 10%, and even more preferably at least about 20%, by weight of the perfume composition, the total level of enduring perfume ingredients, as disclosed herein, being at least about 70%, all by weight of said enduring perfume composition.

Other cyclodextrin-incompatible enduring perfume materials that can be used with the above named enduring perfume ingredients can be characterized by boiling point (B.P.) and octanol/water partitioning coefficient (P). The octanol/water partitioning coefficient of a perfume ingredient is the ratio between its equilibrium concentrations in octanol and in water. These other enduring perfume ingredients of this invention have a molecular weight of more than about 210, preferably more than about 220; and an octanol/water partitioning coefficient P of about 1,000 or higher. Since the partitioning coefficients of these other enduring perfume ingredients of this invention have high values, they are more conveniently given in the form of their logarithm to the base 10, logP. Thus these other enduring perfume ingredients of this invention have logP of about 3 or higher, preferably more than about 3.1, and even more preferably more than about 3.2.

The following table illustrates the molecular weight property of some of the cyclodextrin-incompatible enduring (hydrophobic) perfume materials (i.e. having significant or strong CD interaction) versus cyclodextrin-compatible perfume materials (i.e. having weak CD interaction).

Examples of Perfume Components for CD Interaction

| Perfume component | Molecular weight | CD interaction |
| --- | --- | --- |
| Diethyl Phthalate | 222.0 | weak |
| Methyl Dihydro Jasmonate | 226.3 | weak |
| Lyral | 210.3 | weak |
| Hexyl Salicylate | 222.3 | weak |
| Iso-E Super | 234.0 | weak |
| Hexyl cinnamic Aldehyde | 216.3 | weak |
| Iso-propyl Myristate | 270.0 | weak |
| Galaxolide | 258 | weak |
| Tonalid | 258 | weak |
| Phenyl-Ethyl-Phenyl Acetate | 240 | weak |
| Tetrahydrolinalol | 158.0 | significant |
| Koavone | 182.0 | strong |
| Terpinyl Acetate | 196.0 | significant |
| Vertenex | 198.3 | strong |
| Flor Acetate | 192.0 | strong |
| a-ionone | 192.3 | strong |
| Cymal | 170.0 | strong |
| a-Me Ionone | 206.3 | strong |
| Frutene | 206.0 | strong |
| Lilial | 204.3 | strong |

Nonlimiting examples of other enduring (hydrophobic) perfume materials which tend to be cyclodextrin-incompatible and can be used in the perfume compositions of the present invention are:

Examples of Other Cyclodextrin-Incompatible
Enduring Perfume Materials

| Perfume Ingredients | Approximate B.P. (° C.) (a) | ClogP |
|---|---|---|
| BP ≧ 250° C. and ClogP ≧ 3.0 | | |
| Allyl cyclohexane propionate | 267 | 3.935 |
| Ambrettolide | 300 | 6.261 |
| Ambrox DL (Dodecahydro-3a,6,6,9a-tetramethyl-naphthol[2,1-b]furan) | 250 | 5.400 |
| Amyl benzoate | 262 | 3.417 |
| Amyl cinnamate | 310 | 3.771 |
| Amyl cinnamic aldehyde | 285 | 4.324 |
| Amyl cinnamic aldehyde dimethyl acetal | 300 | 4.033 |
| iso-Amyl salicylate | 277 | 4.601 |
| Aurantiol | 450 | 4.216 |
| Benzophenone | 306 | 3.120 |
| Benzyl salicylate | 300 | 4.383 |
| para-tert-Butyl cyclohexyl acetate | +250 | 4.019 |
| iso-Butyl quinoline | 252 | 4.193 |
| beta-Caryophyllene | 256 | 6.333 |
| Cadinene | 275 | 7.346 |
| Cedrol | 291 | 4.530 |
| Cedryl acetate | 303 | 5.436 |
| Cedryl formate | +250 | 5.070 |
| Cinnamyl cinnamate | 370 | 5.480 |
| Cyclohexyl salicylate | 304 | 5.265 |
| Cyclamen aldehyde | 270 | 3.680 |
| Dihydro isojasmonate | +300 | 3.009 |
| Diphenyl methane | 262 | 4.059 |
| Diphenyl oxide | 252 | 4.240 |
| Dodecalactone | 258 | 4.359 |
| iso E super | +250 | 3.455 |
| Ethylene brassylate | 332 | 4.554 |
| Ethyl methyl phenyl glycidate | 260 | 3.165 |
| Ethyl undecylenale | 264 | 4.888 |
| Exaltolide | 280 | 5.346 |
| Galaxolide | +250 | 5.482 |
| Geranyl anthranilate | 312 | 4.216 |
| Geranyl phenyl acetate | +250 | 5.233 |
| Hexadecanolide | 294 | 6.805 |
| Hexenyl salicylate | 271 | 4.716 |
| Hexyl cinnamic aldehyde | 305 | 5.473 |
| Hexyl salicylate | 290 | 5.260 |
| alpha-Irone | 250 | 3.820 |
| Lilial (p-t-bucinal) | 258 | 3.858 |
| Linalyl benzoate | 263 | 5.233 |
| 2-Methoxy naphthalene | 274 | 3.235 |
| gamma-n-Methyl ionone | 252 | 4.309 |
| Musk indanone | +250 | 5.458 |
| Musk ketone | MP = 137° C. | 3.014 |
| Musk tibetine | MP = 136° C. | 3.831 |
| Myristicin | 276 | 3.200 |
| Oxahexadecanolide-10 | +300 | 4.336 |
| Oxahexadecanolide-11 | MP = 35° C. | 4.336 |
| Patchouli alcohol | 285 | 4.530 |
| Phantolide | 288 | 5.977 |
| Phenyl ethyl benzoate | 300 | 4.058 |
| Phenyl ethyl phenyl acetate | 325 | 3.767 |
| Phenyl heptanol | 261 | 3.478 |
| Phenyl hexanol | 258 | 3.299 |
| alpha-Santalol | 301 | 3.800 |
| Thibetolide | 280 | 6.246 |
| delta-Undecalactone | 290 | 3.830 |
| gamma-Undecalactone | 297 | 4.140 |
| Undecavertol (4-methyl-3-decen-5-ol) | 250 | 3.690 |
| Vetiveryl acetate | 285 | 4.882 |
| Yara-yara | 274 | 3.235 |
| Ylangene | 250 | 6.268 |

(a) M.P. is melting point; these ingredients have a B.P. (boiling point) higher than about 250° C.

The preferred perfume compositions used in the present invention typically contain at least 4 different cyclodextrin-incompatible enduring (hydrophobic) perfume materials, preferably at least 5 different cyclodextrin-incompatible enduring (hydrophobic) perfume materials, more preferably at least 6 different cyclodextrin-incompatible enduring (hydrophobic) perfume materials, and even more preferably at least 7 different cyclodextrin-incompatible enduring (hydrophobic) perfume materials. Most common perfume materials which are derived from natural sources are composed of a multitude of components. When each such material is used in the formulation of the preferred perfume compositions of the present invention, it is counted as one single material, for the purpose of defining the invention.

In order to allow for functionally-available cyclodextrin in the present compositions, the cyclodextrin-incompatible enduring (hydrophobic) perfume materials are preferably processed with other components before the addition of cyclodextrin as described hereinafter in Section H.

7. Cyclodextrin-Compatible Perfume Materials

Hydrophilic perfume materials tend to be cyclodextrin-compatible in aqueous compositions. Cyclodextrin-compatible perfume materials have complexation constants with cyclodextrin of no greater than about 5,000 $M^{-1}$, preferably no greater than about 4,000 $M^{-1}$, and more preferably no greater than about 3,000 $M^{-1}$. Hydrophilic perfumes are composed predominantly of ingredients having a ClogP, as described hereinbefore, of less than about 3.5, more preferably less than about 3.0. If the perfume ingredients are hydrophilic, they should be dissolved in the aqueous phase so they do not complex with the cyclodextrin. It is important to note that for best product stability and improved cyclodextrin compatibility and to maintain functionally-available cyclodextrin, a clear premix consisting of hydrophilic perfume ingredients, cyclodextrin compatible surfactant, and solubility aid (for example, ethanol) is firstly made so that all hydrophilic perfume ingredients are pre-dissolved. Cyclodextrin, water hold and optional ingredients are always added during the final mixing stage. In order to reserve an effective amount of functionally-available cyclodextrin for reducing/removing unwanted molecules, such as malodorous molecules, hydrophilic perfume ingredients are typically present at a level wherein less than about 90% of the cyclodextrin complexes with the perfume, preferably less than about 50% of the cyclodextrin complexes with the perfume, more preferably, less than about 30% of the cyclodextrin complexes with the perfume, and most preferably, less than about 10% of the cyclodextrin complexes with the perfume. The cyclodextrin to perfume weight ratio is preferably greater than about 8:1, more preferably greater than about 10:1, still more preferably greater than about 20:1, even more preferably greater than 40:1 and most preferably greater than about 70:1.

8. Cyclodextrin-Compatible Antimicrobial Actives

A solubilized, water-soluble, cyclodextrin-compatible antimicrobial active, is useful in the present compositions for providing protection against organisms that become attached to the treated material. The antimicrobial should be cyclodextrin-compatible, e.g., not substantially forming complexes with the cyclodextrin in the stable compositions of the present invention. The free, uncomplexed antimicrobial, e.g., antibacterial, active provides an optimum antibacterial performance.

Sanitization of fabrics can be achieved by the compositions of the present invention containing, antimicrobial materials, e.g., antibacterial halogenated compounds, quaternary compounds, and phenolic compounds.

Biguanides. Some of the more robust cyclodextrin-compatible antimicrobial halogenated compounds which can function as disinfectants/sanitizers as well as finish product preservatives (vide intra), and are useful in the compositions of the present invention include 1,1'- hexamethylene bis(5-(p-chlorophenyl)biguanide), commonly known as chlorhexidine, and its salts, e.g., with hydrochloric, acetic and gluconic acids. The digluconate salt is highly water-soluble, about 70% in water, and the diacetate salt has a solubility of about 1.8% in water. When chlorhexidine is used as a sanitizer in the present invention it is typically present at a level of from about 0.001% to about 0.4%, preferably from about 0.002% to about 0.3%, and more preferably from about 0.05% to about 0.2%, by weight of the usage composition. In some cases, a level of from about 1% to about 2% may be needed for virucidal activity.

Other useful biguanide compounds include Cosmoci® CQ®, Vantocil® IB, including poly (hexamethylene biguanide) hydrochloride. Other useful cationic antimicrobial agents include the bis-biguanide alkanes. Usable water soluble salts of the above are chlorides, bromides, sulfates, alkyl sulfonates such as methyl sulfonate and ethyl sulfonate, phenylsulfonates such as p-methylphenyl sulfonates, nitrates, acetates, gluconates, and the like.

Examples of suitable bis biguanide compounds are chlorhexidine; 1,6-bis-(2-ethylhexylbiguanidohexane) dihydrochloride; 1,6-di-($N_1,N_1$'-phenyldiguanido-$N_5,N_5$')-hexane tetrahydrochloride; 1,6-di-($N_1,N_1$'-phenyl-$N_1,N_1$'-methyldiguanido-$N_5,N_5$')-hexane dihydrochloride; 1,6-di ($N_1,N_1$'-o-chlorophenyldiguanido-$N_5,N_5$')-hexane dihydrochloride; 1,6-di($N_1,N_1$'-2,6-dichlorophenyldiguanido-$N_5,N_5$')hexane dihydrochloride; 1,6-di[$N_1,N_1$'-.beta.-(p-methoxyphenyl) diguanido-$N_5,N_5$']-hexane dihydrochloride; 1,6-di[$N_1,N_1$'-.alpha-methyl-.beta.-phenyldiguanido-$N_5,N_5$')-hexane dihydrochloride; 1,6-di ($N_1,N_1$'-p-nitrophenyldiguanido-$N_5,N_5$')hexane dihydrochloride;.omega.:.omega.'-di-($N_1,N_1$'-phenylguanido-$N_5,N_5$')-di-n-propylether dihydrochloride;.omega:omega'-di($N_1,N_1$'-p-chlorophenyldiguanido-$N_5,N_5$')-di-n-propylether tetrahydrochloride; 1,6-di($N_1,N_1$'-2,4-dichlorophenyldiguanido-$N_5,N_5$')hexane tetrahydrochloride; 1,6-di($N_1,N_1$'-p-methylphenyldiguanido-$N_5,N_5$')hexane dihydrochloride; 1,6-di($N_1,N_1$'-2,4,5-trichlorophenyldiguanido-$N_5,N_5$') hexane tetrahydrochloride; 1,6-di[$N_1,N_1$'-.alpha.-(p-chlorophenyl) ethyldiguanido-$N_5,N_5$'] hexane dihydrochloride;.omega.:.omega.'di($N_1$, $N_1$'-p-chlorophenyldiguanido-$N_5,N_5$')m-xylene dihydrochloride; 1,12-di($N_1,N_1$'-p-chlorophenyldiguanido-$N_5,N_5$') dodecane dihydrochloride; 1,10-di($N_1,N_1$'-phenyldiguanido-$N_5,N_5$')-decane tetrahydrochloride; 1,12-di($N_1,N_1$-phenyldiguanido-$N_5,N_5$') dodecane tetrahydrochloride; 1,6-di($N_1,N_1$'-o-chlorophenyldiguanido-$N_5,N_5$') hexane dihydrochloride; 1,6-di($N_1,N_1$'-p-chlorophenyldiguanido-$N_5,N_5$')-hexane tetrahydrochloride; ethylene bis (1-tolyl biguanide); ethylene bis (p-tolyl biguanide); ethylene bis(3,5-dimethylphenyl biguanide); ethylene bis(p-tert-amylphenyl biguanide); ethylene bis(nonylphenyl biguanide); ethylene bis (phenyl biguanide); ethylene bis (N-butylphenyl biguanide); ethylene bis (2,5-diethoxyphenyl biguanide); ethylene bis(2,4-dimethylphenyl biguanide); ethylene bis(o-diphenylbiguanide); ethylene bis(mixed amyl naphthyl biguanide); N-butyl ethylene bis(phenylbiguanide); trimethylene bis(o-tolyl biguanide); N-butyl trimethylene bis (phenyl biguanide); and the corresponding pharmaceutically acceptable salts of all of the above such as the acetates; gluconates; hydrochlorides; hydrobromides; citrates; bisulfites; fluorides; polymaleates; N-coconutalkylsarcosinates; phosphites; hypophosphites; perfluorooctanoates; silicates; sorbates; salicylates; maleates; tartrates; fumarates; ethylenediaminetetraacetates; iminodiacetates; cinnamates; thiocyanates; arginates; pyromellitates; tetracarboxybutyrates; benzoates; glutarates; monofluorophosphates; and perfluoropropionates, and mixtures thereof. Preferred antimicrobials from this group are 1,6-di-($N_1,N_1$'-phenyldiguanido-$N_5,N_5$')hexane tetrahydrochloride; 1,6-di($N_1,N_1$'-chlorophenyldiguanido-$N_5,N_5$')-hexane dihydrochloride; 1,6-di($N_1,N_1$'-2,6-dichlorophenyldiguanido-$N_5,N_5$')hexane dihydrochloride; 1,6-di($N_1,N_1$'-2,4-dichlorophenyldiguanido-$N_5,N_5$')hexane tetrahydrochloride; 1,6-di[$N_1,N_1$'-.alpha.-(p-chlorophenyl) ethyldiguanido-$N_5,N_5$'] hexane dihydrochloride;.omega.:.omega.'di($N_1,N_1$'-p-chlorophenyldiguanido-$N_5,N_5$')m-xylene dihydrochloride; 1,12-di($N_1,N_1$'-p-chlorophenyldiguanido-$N_5,N_5$') dodecane dihydrochloride; 1,6-di($N_1,N_1$'-o-chlorophenyldiguanido-$N_5,N_5$') hexane dihydrochloride; 1,6di($N_1,N_1$'-p-chlorophenyldiguanido-$N_5,N_5$')-hexane tetrahydrochloride; and mixtures thereof; more preferably, 1,6-di($N_1,N_1$'-o-chlorophenyldiguanido-$N_5,N_5$')-hexane dihydrochloride; 1,6-di($N_1,N_1$'-2,6-dichlorophenyldiguanido-$N_5,N_5$')hexane dihydrochloride; 1,6-di($N_1,N_1$'-2,4-dichlorophenyldiguanido-$N_5,N_5$')hexane tetrahydrochloride; 1,6-di($N_1,N_1$'-.alpha.-p-chlorophenyl) ethyldiguanido-$N_5,N_5$'] hexane dihydrochloride;.omega.:.omega.'di($N_1,N_1$'-p-chlorophenyldiguanido-$N_5$, $N_5$')m-xylene dihydrochloride; 1,12-di($N_1,N_1$'-p-chlorophenyldiguanido-$N_5,N_5$) dodecane dihydrochloride; 1,6-di($N_1,N_1$'-o-chlorophenyldiguanido-$N_5,N_5$) hexane dihydrochloride; 1,6-di($N_1,N_1$-p-chlorophenyldiguanido-$N_5,N_5$)-hexane tetrahydrochloride; and mixtures thereof. As stated hereinbefore, the bis biguanide of choice is chlorhexidine its salts, e.g., digluconate, dihydrochloride, diacetate, and mixtures thereof.

Quaternary Compounds. A wide range of quaternary compounds can also be used as antimicrobial actives, in conjunction with the preferred surfactants, for compositions of the present invention that do not contain cyclodextrin. Non-limiting examples of useful quaternary compounds include: (1) benzalkonium chlorides and/or substituted benzalkonium chlorides such as commercially available Barquat® (available from Lonza), Maquat® (available from Mason), Variquat® (available from Witco/Sherex), and Hyamine® (available from Lonza); (2) di($C_6$–$C_{14}$)alkyl di short chain ($C_{1-4}$ alkyl and/or hydroxyalkl) quaternary such as Bardac® products of Lonza, (3) N-(3-chloroallyl) hexaminium chlorides such as Dowicide® and Dowicil® available from Dow; (4) benzethonium chloride such as Hyamine® 1622 from Rohm & Haas; (5) methylbenzethonium chloride represented by Hyamine® 10X supplied by Rohm & Haas, (6) cetylpyridinium chloride such as Cepacol chloride available from of Merrell Labs. Examples of the preferred dialkyl quaternary compounds are di($C_8$–$C_{12}$) dialkyl dimethyl ammonium chloride, such as didecyidimethylammonium chloride (Bardac 22), and dioctyidimethylammonium chloride (Bardac 2050). Typical concentrations for biocidal effectiveness of these quaternary compounds range from about 0.001% to about 0.8%, preferably from about 0.005% to about 0.3%, more preferably from about 0.01% to about 0.2%, and even more preferably from about 0.03% to about 0.1%, by weight of the usage composition. The corresponding concentrations for the concentrated compositions are from about 0.003% to about about 2%, preferably from about 0.006% to about 1.2%, and more preferably from about 0.1% to about 0.8% by weight of the concentrated compositions.

Surfactants, when added to the antimicrobials tend to provide improved antimicrobial action. This is especially true for the siloxane surfactants, and especially when the siloxane surfactants are combined with the chlorhexidine antimicrobial actives.

9. Cyclodextrin-Incompatible Skin Conditioning Agents

Compositions of the invention can further comprise a safe and effective amount of a cyclodextrin-incompatible skin conditioning agent. The cyclodextrin-incompatible skin conditioning agent is useful in skin moisturizing compositions for lubricating the skin, increasing the smoothness and suppleness of the skin, preventing or relieving dryness of the skin, hydrating the skin, and/or protecting the skin. The skin conditioning agent enhances the skin appearance benefits provided by components of the composition. The cyclodextrin-incompatible skin conditioning agent is preferably selected from the group consisting of emollients, humectants, moisturizers and mixtures thereof. The cyclodextrin-incompatible skin conditioning agent is typically present at a level of at least about 0.1%, more preferably from about 1% to about 99%, even more preferably from about 1% to about 50%, still more preferably from about 2% to about 30% and most preferably from about 5% to about 25% (e.g., about 5% to about 10% or 15%). The cyclodextrin-incompatible skin conditioning agents of the present invention have complexation constants with cyclodextrin of greater than about 5,000 M-1, preferably greater than about 8,000 $M^{-1}$, and more preferably greater than about 10,000 $M^{-1}$.

A variety of emollients can be employed. These emollients may be selected from one or more of the following classes: Triglyceride esters; Acetoglyceride esters; Alkyl esters of fatty acids having 10 to 20 carbon atoms; Alkenyl esters of fatty acids having 10 to 20 carbon atoms; Fatty acids having 10 to 20 carbon atoms; Fatty alcohols having 10 to 20 carbon atoms; Lanolin and lanolin derivatives; Polyhydric alcohol esters; Wax esters; Beeswax derivatives; Vegetable waxes; Phospholipids; Sterols including, but not limited to, cholesterol and cholesterol fatty acid esters; and Amides.

Additional types of cyclodextrin-incompatible skin conditioning agents include humectants of the polyhydric alcohol-type. Also useful herein are guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); sugar and starch derivatives (e.g., alkoxylated glucose); hyaluronic acid and derivatives thereof (e.g., salt derivatives such as sodium hyaluraonate); lactamide monoethanolamine; acetamide monoethanolamine; urea; panthenol; sugars; starches; silicone gums; and mixtures thereof. Also useful are the propoxylated glycerols described in U.S. Pat. No. 4,976,953, which is description is incorporated herein by reference. Other useful conditioning agents include the various $C_1$–$C_{30}$ monoesters and polyesters of sugars and related materials such as described herein in reference to the hydrophobic component.

Suitable cyclodextrin-incompatible skin conditioning agents are described in more detail in U.S. Pat. No. 6,001,377 issued Dec. 14, 1999 to SaNogueira, Jr. et al., which is incorporated herein by reference.

10. Other Ingredients

Other optional ingredients particularly suitable in the present compositions are described in the following, which are hereby incorporated herein by reference: U.S. Pat. No. 5,714,137 issued Feb. 3, 1998 to Trinh et al.; U.S. Pat. No. 5,942,217 issued Aug. 24, 1999 to Woo et al.; U.S. Pat. No. 6,001,343 issued Dec. 14, 1999 to Trinh et al.; International Application No. PCT/US98/08124, filed Apr. 27, 1998, and published Nov. 4, 1999 as WO99/55816 by Woo et al. (P&G Case 7097); International Application No. PCT/US98/08129, filed Apr. 27, 1998, and published Nov. 4, 1999 as WO99/55950 by Hubesch et al. (P&G Case CM-1714).

II. Process of Manufacture

Compositions of the present invention that comprise low-degree of substitution cyclodextrin derivatives can be manufactured by combining and/or mixing together the components of the composition.

When the present compositions comprise low-degree of substitution cyclodextnn derivatives, cyclodextrin-incompatible material, and cyclodextrin-compatible material, the process of manufacturing the present compositions can be important to provide the preferred functionally-available cyclodextrin in the compositions. To maintain functionally-available cyclodextrin in the composition, the present compositions can be made by first combining cyclodextrin-incompatible materials together with cyclodextrin-compatible surfactant. This results in the formation of molecular aggregates, such as miscelles or vesicles, in which the cyclodextrin-incompatible materials are maintained. Only after the cyclodextrin-incompatible materials are combined with cyclodextrin-compatible surfactant, is the cyclodextrin added to form the present compositions. As a result, the compositions have functionally-available cyclodextrin due to the tendency of the cyclodextrin-incompatible materials to remain within the molecular aggregates that they form with cyclodextrin-compatible surfactant, effectively keeping the cyclodextrin-incompatible materials away from the cavities of the cyclodextrin molecules. This allows for functionally-available cyclodextrin in the present compositions.

When the present compositions comprise functionally-available cyclodextrin, cyclodextrin-incompatible material, and cyclodextrin-compatible material, the present process of manufacturing a composition suitable for capturing unwanted molecules comprises the steps of:

(a) providing cyclodextrin, a cyclodextrin-compatible material, and a cyclodextrin-incompatible material;

(b) combining said cyclodextrin-compatible material and said cyclodextrin-incompatible material to form a first mixture; and (c) subsequently combining said cyclodextrin with said first mixture to form said composition suitable for capturing unwanted molecules.

The components utilized in the present processes of manufacture, as well as the compositions produced by the processes, are described hereinbefore. The processes can also comprise combining the cyclodextrin-compatible material and the cyclodextrin-incompatible material with water to form a first aqueous mixture and subsequently adding cyclodextrin to the first aqueous mixture to form the composition suitable for capturing unwanted molecules. The present processes can also comprise combining the cyclodextrin-compatible material and the cyclodextrin-incompatible material to form a first mixture, combining the cyclodextrin with water to form a second aqueous mixture and combining the first mixture and the second aqueous mixture to form the composition suitable for capturing unwanted molecules.

III. Methods of Use

The stable compositions of the present invention comprising low-degree of substitution cyclodextrin are suitable for removing unwanted molecules, such as malodorous molecules, from surfaces, especially inanimate surfaces including fabrics, including carpets, and household surfaces such as countertops, dishes, floors, garbage cans, ceilings, walls, carpet padding, air filters, and the like, and animate surfaces, including skin, hair, and the like. The method of the present invention comprises contacting a surface containing unwanted molecules with a stable composition comprising functionally-available cyclodextrin and a cyclodextrin-incompatible material. As used herein, the term "unwanted molecules" refers to molecules that are desirably reduced or removed from surfaces for aesthetic or safety reasons, such as malodorous molecules.

Unwanted molecules have a relatively strong tendency to complex with cyclodextrin, such that when the present compositions comprising functionally-available cyclodextrin come in contact with the unwanted molecules, the unwanted molecules will complex with the functionally-available cyclodextrin which effectively removes or reduces the presence of the unwanted molecules on the treated surface. Unwanted molecules complex with the functionally-available cyclodextrin either by simply complexing with uncomplexed cyclodextrin in the present compositions, or by replacing molecules that are weakly complexed with the functionally-available cyclodextrin due to the stronger affinity of the cyclodextrin to complex with the unwanted molecules. In this instance, a replacement occurs wherein the weakly complexed molecule is replaced by the unwanted molecule in the cavity of the functionally-available cyclodextrin. As such, the unwanted molecules, or mixtures thereof, generally, and preferably, have a complexation constant that is greater than the complexation constant of molecules that are weakly complexed with cyclodextrin in the present compositions.

The present compositions can contain components which make them suitable for a variety of applications, including but not limited to, laundry detergent compositions, fabric softening compositions, hard surface cleaning compositions, dishwashing detergent compositions, malodor controlling compositions, shampoo compositions, hair conditioner compositions, personal cleansing compositions, underarm deodorant compositions, and the like.

For controlling odor on fabrics, especially dry fabrics, the present compositions are preferably used as a spray. It is preferable that the usage compositions of the present invention contain low levels of cyclodextrin so that a visible stain does not appear on the fabric at normal usage levels. Preferably, the solution used to treat the surface under usage conditions is virtually not discernible when dry. Typical levels of total cyclodextrin in usage compositions for usage conditions are from about 0.01% to about 5%, preferably from about 0.1% to about 4%, more preferably from about 0.5% to about 2% by weight of the composition. Usage compositions will typically have at least about 0.001%, preferably at least about 0.01%, and more preferably at least about 0.1%, by weight of the composition of functionally-available cyclodextrin. Compositions with higher concentrations can leave unacceptable visible stains on fabrics as the solution evaporates off of the fabric. This is especially a problem on thin, colored, synthetic fabrics. In order to avoid or minimize the occurrence of fabric staining, it is preferable that the fabric be treated at a level of less than about 5 mg of cyclodextrin per gram of fabric, more preferably less than about 2 mg of cyclodextrin per gram of fabric. The presence of a surfactant can improve appearance by minimizing localized spotting.

IV. Test Methods

A. Measurement Of Complexation Constants

A spectral displacement method with phenolphthalein is used to determine the complexation constant between cyclodextrin and a given material, especially for surfactants. This method of determining complexation constants with cyclodextrins is described in detail in the following references, which are hereby incorporated herein by reference: Sasaki, K. J., Christian, S. D., and Tucker, E. E., "Study of the Stability of 1:1 Complexes Between Aliphatic Alcohols and b-Cyclodextrins in Aqueous Solution," *Fluid Phase Equilibria*, Vol. 49, (Amsterdam, Elsevier Science Publishers, 1989), pp. 281–89; and Wilson, L. D., Siddall, S. R., and Verrall R. E., "A Spectral Displacement Study of the Binding Constants of Cyclodextrin-Hydrocarbon and -Fluorocarbon Surfactant Inclusion Complexes," *Canadian Journal of Chemistry*, Vol. 75, (NRC Canada 1997), pp. 927–933.

The complexation constant of a given material with cyclodextrin is obtained by an absorbance measurement in the visible region at 550 nm that is performed with a spectrophotometer at room temperature. All solutions are prepared in $4.0 \times 10^{-3}$ mol/l $Na_2CO_3$ solution to maintain a constant pH. The concentration of phenolphthalein is kept constant at $3.0 \times 10^{-5}$ mol/l. Cyclodextrin concentration and surfactant concentration are varied. Here, optimum parameter values for absorption coefficient of phenolphthalein at 550 nm is 33,000 $M^{-1}$ $cm^{-1}$, and the complexation constants of phenolphthalein with cyclodextrin and cyclodextrin derivatives are preliminary obtained. For example, the complexation constant of phenolphthalein with beta-cyclodextrin is about 21.000 $M^{-1}$. Complexation constants of cyclodextrin-compatible and/or cyclodextrin-incompatible materials are determined with using the free, uncomplexed phenolphthalein concentration obtained by absorbance at 550 nm.

B. Malodor Performance Test

This test method is used to evaluate the effectiveness of a composition in reducing or removing malodor from fabrics. The test fabrics are first washed in a laundry washer using unscented laundry detergent and then dried in a laundry dryer. About 80 microliters of a synthetic body malodor composition is uniformly applied over a two square inch area of each test fabric. The malodor-treated test fabrics are then sealed in a plastic bag and allowed to equilibrate overnight at ambient temperature. Qualified odor graders evaluate the initial malodor level of the malodor-treated test fabrics and assign a malodor grade according to the Malodor Evaluation Scale below. The malodor-treated test fabrics are then treated with equivalent amounts of the test compositions by spraying the test compositions onto the test fabrics and allowing the test fabrics to dry. Once the test fabrics have dried, the qualified odor graders again evaluate the malodor level of the test fabrics and assign a malodor grade according to the Malodor Evaluation Scale below. Initial malodor grades and after-treatment malodor grades are recorded and the differences between the grades are calculated to establish the "Malodor Reduction" value.

| Malodor Evaluation Scale | |
|---|---|
| 0 | No Malodor/Perfume Present |
| 10 | I Think There is Malodor/Perfume Present |
| 25 | Slight Malodor/Perfume Present |
| 50 | Moderate Malodor/Perfume Present |
| 75 | Strong Malodor/Perfume Present |
| 100 | Extremely Strong Malodor/Perfume Present |

EXAMPLE I

The following compositions are evaluated according to the Malodor Performance Test described hereinbefore in Section IV.B:

|  | COMPOSITION | | | |
|---|---|---|---|---|
| INGREDIENTS (WT %) | A | B | C | D |
| 5.5 DOS HPBCD[1] | 1.0 | — | — | 0.4 |
| 3.3 DOS HPBCD[2] | — | 0.5 | 1.0 | — |
| BCD[3] | — | — | — | 0.1 |
| SILWET L-7600 | 0.1 | 0.1 | 0.1 | 0.1 |
| Sodium Polyacrylate (2500 MW) | 0.1 | 0.1 | 0.1 | 0.1 |
| Diethylene Glycol | 0.25 | 0.25 | 0.25 | 0.25 |
| Ethanol | 3.0 | 3.0 | 3.0 | 3.0 |
| KATHON (Preservative) | 3 ppm | 3 ppm | 3 ppm | 3 ppm |
| Perfume | 0.1 | 0.1 | 0.1 | 0.1 |
| Distilled Water | Balance | Balance | Balance | Balance |

|  | COMPOSITION | | | |
|---|---|---|---|---|
| INGREDIENT (WT %) | E | F | G | H |
| 5.5 DOS HPBCD[1] | 0.75 | — | — | — |
| 3.3 DOS HPBCD[2] | — | 0.75 | — | — |
| 12.25 DOS MeBCD[4] | — | — | 0.75 | — |
| 4.2 DOS MeBCD[5] | — | — | — | 0.75 |
| POE-60 (Hydrogenated Caster Oil) | 0.2 | 0.2 | 0.2 | 0.2 |
| SILWET L-77 | 0.2 | 0.2 | 0.2 | 0.2 |
| Sodium Polyacrylate (2500 MW) | 0.1 | 0.1 | 0.1 | 0.1 |
| KATHON (Preservative) | 3 ppm | 3 ppm | 3 ppm | 3 ppm |
| Perfume | 0.06 | 0.06 | 0.06 | 0.06 |
| Distilled Water | Balance | Balance | Balance | Balance |

[1] Hydroxypropyl beta-cyclodextrin having an average degree of substitution of 5.5.
[2] Hydroxypropyl beta-cyclodextrin having an average degree of substitution of 3.3.
[3] Non-derivatized beta-cyclodextrin.
[4] Methylated beta-cyclodextrin having an average degree of substitution of 12.25.
[5] Methylated beta-cyclodextrin having an average degree of substitution of 4.2.

Compositions A–D are tested according to the Malodor Performance Test and the results are reported in the following table:

| COMPOSITION | INITIAL MALODOR GRADE | MALODOR GRADE AFTER TREATMENT | MALODOR REDUCTION VALUE |
|---|---|---|---|
| A | 80 | 50 | 30 |
| B | 85 | 35 | 50 |
| C | 85 | 35 | 50 |
| D | 85 | 30 | 55 |

These results show that compositions comprising low-degree of substitution cyclodextrin derivatives (e.g. Compositions B and C) or cyclodextrin mixtures (e.g. Composition D) exhibit significantly improved performance in regard to capturing unwanted molecules, such as malodorous molecules, as compared to compositions comprising cyclodextrin derivatives having a higher average degree of substitution (e.g. Composition A).

Compositions E–H are tested according to the Malodor Performance Test and the results are reported in the following table:

| COMPOSITION | AVERAGE MALODOR REDUCTION VALUE |
|---|---|
| E | 37.1 |
| F | 45.7 |
| G | 42.5 |
| H | 55 |

These results show that compositions comprising low-degree of substitution cyclodextrin derivatives exhibit significantly improved performance in regard to capturing unwanted molecules, such as malodorous molecules, as compared to compositions comprising cyclodextrin derivatives having a higher average degree of substitution (comparing Composition E vs. F and Composition G vs. H).

EXAMPLE II

The following are additional non-limiting Examples of the compositions of the present invention.

| Examples Ingredients | I Wt % | J Wt % | K Wt % | L Wt % | M Wt % |
|---|---|---|---|---|---|
| 5.5 DOS HPBCD[1] | 0.5 | — | 0.25 | — | 0.35 |
| 4.2 DOS MeBCD[5] | — | 0.25 | — | 0.5 | — |
| Cartaretin F-23[6] | 1.0 | — | — | — | — |
| Copolymer 937[7] | — | 0.3 | — | — | — |
| Copolymer 958[8] | — | — | 0.4 | — | — |
| Diaformer Z-SM[9] | — | — | — | 0.5 | — |
| Vinex 2019[10] | — | — | — | — | 0.5 |
| D5 volatile silicone | 0.25 | — | 0.5 | 0.2 | — |
| PDMS 10,000 csi | — | 0.25 | — | 0.2 | — |
| Silwet L-7600 | 0.3 | — | — | — | 0.1 |
| Silwet L-7602 | — | 0.25 | — | 0.4 | — |
| Silwet L-7622 | — | — | 0.5 | — | — |
| Diethylene glycol | — | — | 0.2 | — | — |
| Propylene glycol | 0.06 | — | — | — | 0.1 |
| Perfume | 0.1 | 0.05 | 0.05 | 0.1 | 0.05 |
| Kathon | 3 ppm | 3 ppm | 3 ppm | 3 ppm | 3 ppm |
| Distilled water | Bal. | Bal. | Bal. | Bal. | Bal. |

[1] Hydroxypropyl beta-cyclodextrin having an average degree of substitution of 5.5.
[5] Methylated beta-cyclodextrin having an average degree of substitution of 4.2.
[6] Adipic acid/dimethylaminohydroxypropyl diethylenetriamine copolymer.
[7] Polyvinylpyrrolidone/dimethylaminoethyl methacrylate copolymer.
[8] Polyvinylpyrrolidone/dimethylaminoethyl methacrylate copolymer.
[9] Methacryloyl ethyl betaine/methacrylates copolymer.
[10] Polyvinyl alcohol copolymer resin.

What is claimed is:

1. A composition for capturing unwanted molecules, said composition comprising low degree of substitution cyclodextrin derivative and a perfume material wherein said low-degree of substitution cyclodextrin derivative is selected from the group consisting of hydroxyalkyl cyclodextrin having an average degree of substitution of less than about 4.5, alkylated cyclodextrin having an average degree of substitution of less than about 6.0, and mixtures thereof.

2. A composition according to claim 1 wherein said low-degree of substitution cyclodextrin derivative is selected from the group consisting of hydroxyalkyl cyclodextrin having an average degree of substitution of less than about 4.5, alkylated cyclodextrin having an average degree of substitution of less than about 5.5, and mixtures thereof.

3. A composition for capturing unwanted molecules, said composition comprising low-degree of substitution cyclodextrin derivative and a perfume material wherein said low-degree of substitution cyclodextrin derivative is selected from the group consisting of beta-cyclodextrin derivatives, gamma-cyclodextrin derivatives, and mixtures thereof wherein said beta-cyclodextrin derivative is selected from a hydroxyalkyl beta-cyclodextrin having an average degree of substitution of less than about 4.0, a hydroxypropyl beta-cyclodextrin having an average degree of substitution of about 3.3 an alkylated-beta-cyclodextrin having an average degree of substitution of less than about 6.0, and mixtures thereof.

4. A composition according to claim 3 wherein said alkylated beta-cyclodextrin is methylated beta-cyclodextrin having an average degree of substitution of about 4.2.

5. A composition according to claim 1 wherein said composition further comprises non-derivatized cyclodextrin selected from the group consisting of alpha-cyclodextrin, beta-cyclodextrin, gamma-cyclodextrin, and mixtures thereof.

6. A composition for capturing unwanted molecules, said composition comprising a cyclodextrin mixture comprising a cyclodextrin derivative having an average degree of substitution greater than that of low-degree of substitution cyclodextrin derivative, and either a low-degree of substitution cyclodextrin derivative or a non-derivatized cyclodextrin, wherein the cyclodextrin mixture effectively has an average degree of substitution equal to that of a low-degree of substitution cyclodextrin derivative and further, wherein said cyclodextrin derivative is selected from the group consisting of methylated cyclodextrins, ethylated cyclodextrins, cyclodextrins with hydroxyalkyl groups, branched cyclodextrins, cationic cyclodextrins, anionic cyclodextrins, amphoteric cyclodextrins and cyclodextrins wherein at least one glucopyranose unit has a 3,6-anhydro-cyclomalto structure.

7. A process of manufacturing a composition suitable for capturing unwanted molecules comprising the steps of:
(a) providing low-degree of substitution cyclodextrin wherein said cyclodextrin is selected from the group consisting of methylated cyclodextrins, ethylated cyclodextrins, cyclodextrins with hydroxyalkyl groups, branched cyclodextrins, cationic cyclodextrins, anionic cyclodextrins, amphoteric cyclodextrins and cyclodextrins wherein at feast one glucopyranose unit has a 3,6-anhydro-cyclomalto structure a cyclodextrin-compatible surfactant, and a cyclodextrin-incompatible surfactant;
(b) combining said cyclodextrin-compatible surfactant and said cyclodextrin-incompatible surfactant to form a first mixture; and
(c) subsequently combining said low-degree of substitution cyclodextrin with said first mixture to form said composition suitable for capturing unwanted molecules.

8. A process according to claim 7 wherein said process comprises combining said cyclodextrin-compatible surfactant and said cyclodextrin-incompatible surfactant with water to form a first aqueous mixture and subsequently adding low-degree of substitution cyclodextrin to said first aquous mixture to form said composition suitable for capturing unwanted molecules.

9. A process according to claim 7 wherein said process comprises combining said cyclodextrin-compatible surfactant and said cyclodextrin-incompatible surfactant to form a first mixture, combining said low-degree of substitution cyclodextrin with water to form a second aqueous mixture and combining the first mixture and the second aqueous mixture to form said composition suitable for capturing unwanted molecules.

10. A process according to claim 7 wherein said first mixture comprises said cyclodextrin-incompatible surfactant solubilised in micelles or vesicles comprising said cyclodextrin-compatible surfactant as molecular aggregates.

11. A method of capturing unwanted molecules from a surface comprising applying to the surface a composition comprising low-degree of substitution cyclodextrin derivative and allowing the composition to dry wherein said low-degree of substitution cyclodextrin derivative is selected from the group consisting of hydroxyalkyl cyclodextrin having an average degree of substitution of less than about 4.5, alkylated cyclodextrin having an average degree of substitution of less than about 6.0, and mixtures thereof.

12. The method of claim 11, wherein the composition further comprises a perfume material.

13. The method of claim 11, wherein said low-degree of substitution cyclodextrin derivative is selected from the group consisting of hydroxyalkyl cyclodextrin having an average degree of substitution of less than about 4.5, alkylated cyclodextrin having an average degree of substitution of less fan about 5.5, and mixtures thereof.

14. A method of capturing unwanted molecules from a surface comprising applying to the sure a composition comprising low-degree of substitution cyclodextrin derivative and allowing the composition to dry, wherein said low-degree of substitution cyclodextrin derivative is selected from the group consisting of beta-cyclodextrin derivatives, gamma-cyclodextrin derivatives, and mixtures thereof wherein said beta-cyclodextrin derivative is selected from a hydroxyalkyl beta-cyclodextrin having an average degree of substitution of less than about 4.0, a hydroxypropyl beta-cyclodextrin having an average degree of substitution of about 3.3, an alkylated-beta-cyclodextrin having an average degree of substitution of less than about 6.0, and mixtures thereof.

15. The method of claim 14, wherein said alkylated beta-cyclodextrin is methylated beta-cyclodextrin having an average degree of substitution of about 4.2.

16. The method of claim 11, wherein said composition further comprises non-derivatized cyclodextrin selected from the group consisting of alpha-cyclodextrin, beta-cyclodextrin, gamma-cyclodextrin, and mixtures thereof.

* * * * *